US012226568B2

(12) United States Patent
Sigmon, Jr. et al.

(10) Patent No.: US 12,226,568 B2
(45) Date of Patent: Feb. 18, 2025

(54) MEDICAL SCOPES FOR DELIVERING THERAPEUTIC AGENTS

(71) Applicant: COOK MEDICAL TECHNOLOGIES LLC, Bloomington, IN (US)

(72) Inventors: John Crowder Sigmon, Jr., Winston-Salem, NC (US); Shaun D. Gittard, Winston-Salem, NC (US); Christopher A. Carruthers, Winston-Salem, NC (US); Liam Breen, Ballina (IE); Vihar C. Surti, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 290 days.

(21) Appl. No.: 17/338,198

(22) Filed: Jun. 3, 2021

(65) Prior Publication Data
US 2021/0379302 A1 Dec. 9, 2021

Related U.S. Application Data

(60) Provisional application No. 63/035,270, filed on Jun. 5, 2020.

(51) Int. Cl.
*A61M 13/00* (2006.01)
*A61J 1/20* (2006.01)

(52) U.S. Cl.
CPC ............ *A61M 13/00* (2013.01); *A61J 1/2037* (2015.05); *A61J 1/2058* (2015.05); *A61J 1/2065* (2015.05);
(Continued)

(58) Field of Classification Search
CPC ....... A61B 1/015; A61B 1/00154; A61B 1/05; A61B 1/07; A61B 1/00066; A61B 1/005;
(Continued)

(56) References Cited

U.S. PATENT DOCUMENTS 39,678 A 8/1863 Russell
170,182 A 11/1875 Molesworth
(Continued)

FOREIGN PATENT DOCUMENTS

AU 9382598 3/1999
AU 2009244462 11/2009
(Continued)

OTHER PUBLICATIONS

Hemospray Endoscopic Hemostat Brochure, Cook, Jun. 2018 ESC-D43196-EN-F.
(Continued)

*Primary Examiner* — Scott J Medway
*Assistant Examiner* — Anh Bui
(74) *Attorney, Agent, or Firm* — Vivacqua Crane, PLLC

(57) ABSTRACT

The present embodiments provide systems and methods suitable for delivering a therapeutic agent to a target site. In one example, the system comprises a container for holding the therapeutic agent, and a pressure source having pressurized fluid, wherein the pressure source is in selective fluid communication with at least a portion of the container. A catheter is placed in fluid communication with the container, and has a lumen sized for delivery of the therapeutic agent to a target site. A housing is configured to securely retain the container. The system further comprises a camera having a camera head coupled to the catheter, wherein the camera provides a visual image of the target site during delivery of the therapeutic agent.

14 Claims, 17 Drawing Sheets

(52) U.S. Cl.
CPC .............. *A61M 2202/0225* (2013.01); *A61M 2202/064* (2013.01); *A61M 2205/583* (2013.01)

(58) Field of Classification Search
CPC .............. A61B 1/0052; A61B 1/0684; A61B 2017/003; A61B 2017/007; A61B 2218/002
See application file for complete search history.

(56) References Cited

U.S. PATENT DOCUMENTS

| | | |
|---|---|---|
| 280,202 A | 6/1883 | Mattson |
| 442,785 A | 12/1890 | Schoettl |
| 460,458 A | 9/1891 | Bates |
| 471,865 A | 3/1892 | Howard |
| 533,489 A | 2/1895 | Ogram |
| 566,411 A | 8/1896 | Schoene |
| 576,437 A | 2/1897 | Elliot |
| 693,587 A | 2/1902 | Campbell |
| 775,985 A | 11/1904 | McKain |
| 881,238 A | 3/1908 | Hasbrouck |
| 904,149 A | 11/1908 | Rachmann |
| 938,648 A | 11/1909 | DeVilbiss |
| 1,022,601 A | 4/1912 | Rumberg et al. |
| 1,114,114 A | 10/1914 | Cochenour |
| 1,145,520 A | 7/1915 | Smith |
| 1,261,503 A | 4/1918 | Figgis |
| 1,357,452 A | 11/1920 | Hall |
| 1,466,119 A | 8/1923 | Claflin |
| 1,521,396 A | 12/1924 | Scott |
| 1,685,280 A | 9/1928 | Findley |
| 1,934,793 A | 11/1933 | Crain et al. |
| 2,004,402 A | 6/1935 | Conklin |
| 2,151,418 A | 3/1939 | Bolte |
| 2,223,611 A | 12/1940 | Gross |
| 2,307,986 A | 1/1943 | Bolte et al. |
| 2,390,313 A | 12/1945 | Macgill |
| 2,507,702 A | 5/1950 | Fields |
| 2,519,555 A | 8/1950 | Fields |
| 2,609,155 A | 9/1952 | Fosnaugh |
| 2,632,444 A | 3/1953 | Kas |
| 2,805,013 A | 9/1957 | Cordis |
| 2,934,314 A | 4/1960 | Chambers et al. |
| 2,956,579 A | 10/1960 | Moore et al. |
| 3,016,895 A | 1/1962 | Sein et al. |
| 3,050,261 A | 8/1962 | Littlefield |
| 3,207,618 A | 9/1965 | De Hart |
| 3,506,008 A | 4/1970 | Huck |
| 3,540,444 A | 11/1970 | Moreland |
| 3,572,335 A | 3/1971 | Robinson |
| 3,589,363 A | 6/1971 | Banko et al. |
| 3,599,866 A | 8/1971 | Bolton |
| 3,632,046 A | 1/1972 | Hengesbach |
| 3,647,143 A | 3/1972 | Gauthier et al. |
| 3,649,299 A | 3/1972 | Sholl |
| 3,667,465 A | 6/1972 | Voss |
| 3,710,400 A | 1/1973 | Sparks |
| 3,742,955 A | 7/1973 | Battista et al. |
| 3,744,493 A | 7/1973 | Booher et al. |
| 3,762,410 A | 10/1973 | Bindel |
| 3,788,315 A | 1/1974 | Laurens |
| 3,815,595 A | 6/1974 | Bar |
| 3,900,022 A | 8/1975 | Widran |
| 3,916,896 A | 11/1975 | Ballard |
| 4,009,637 A | 3/1977 | Bittner |
| 4,017,007 A | 4/1977 | Riccio |
| 4,040,420 A | 8/1977 | Speer |
| 4,174,811 A | 11/1979 | Binder et al. |
| 4,184,258 A | 1/1980 | Barrington et al. |
| 4,204,539 A | 5/1980 | Van Brugge |
| 4,204,645 A | 5/1980 | Hopp |
| 4,210,140 A | 7/1980 | James et al. |
| 4,359,049 A | 11/1982 | Redl et al. |
| 4,391,276 A | 7/1983 | Lazarus et al. |
| 4,423,727 A | 1/1984 | Widran et al. |
| 4,427,450 A | 1/1984 | Kostansek |
| 4,427,650 A | 1/1984 | Stroetmann |
| 4,516,442 A | 5/1985 | Davis |
| 4,534,345 A | 8/1985 | Wetterlin |
| 4,539,716 A | 9/1985 | Bell |
| 4,552,556 A | 11/1985 | Urquhart et al. |
| 4,578,067 A | 3/1986 | Cruz, Jr. |
| 4,594,987 A | 6/1986 | Wataya et al. |
| 4,606,501 A | 8/1986 | Bate et al. |
| 4,620,847 A | 11/1986 | Shishov et al. |
| 4,631,055 A | 12/1986 | Redl et al. |
| 4,637,816 A | 1/1987 | Mann |
| H257 H | 4/1987 | Barditch et al. |
| 4,655,211 A | 4/1987 | Sakamoto et al. |
| 4,657,536 A | 4/1987 | Dorman |
| 4,735,616 A | 4/1988 | Eibl et al. |
| 4,738,658 A | 4/1988 | Magro et al. |
| 4,738,740 A | 4/1988 | Pinchuk |
| 4,752,466 A | 6/1988 | Saferstein et al. |
| 4,790,819 A | 12/1988 | Li et al. |
| 4,798,606 A | 1/1989 | Pinchuk |
| 4,803,977 A | 2/1989 | Kremer, Jr. |
| 4,846,405 A | 7/1989 | Zimmermann |
| 4,850,355 A | 7/1989 | Brooks et al. |
| D303,139 S | 8/1989 | Morgan |
| 4,872,450 A | 10/1989 | Austad |
| 4,874,368 A | 10/1989 | Miller et al. |
| 4,890,612 A | 1/1990 | Kensey |
| 4,900,303 A | 2/1990 | Lemelson |
| 4,902,278 A | 2/1990 | Maget et al. |
| 4,902,281 A | 2/1990 | Avoy |
| 4,927,410 A | 5/1990 | Kovacs |
| 4,929,246 A | 5/1990 | Sinofsky |
| 4,941,874 A | 7/1990 | Sandow et al. |
| 4,941,880 A | 7/1990 | Burns |
| 4,945,050 A | 7/1990 | Sanford et al. |
| 4,946,870 A | 8/1990 | Partain, III et al. |
| 4,950,234 A | 8/1990 | Fujioka et al. |
| 4,969,874 A | 11/1990 | Michel et al. |
| 4,978,336 A | 12/1990 | Capozzi et al. |
| 4,994,028 A | 2/1991 | Leonard et al. |
| 5,009,637 A | 4/1991 | Newman et al. |
| 5,015,580 A | 5/1991 | Christou et al. |
| 5,021,059 A | 6/1991 | Kensey et al. |
| 5,053,000 A | 10/1991 | Booth et al. |
| 5,059,187 A | 10/1991 | Sperry et al. |
| 5,061,180 A | 10/1991 | Wiele |
| 5,063,025 A | 11/1991 | Ito |
| 5,064,413 A | 11/1991 | McKinnon et al. |
| 5,106,370 A | 4/1992 | Stewart |
| 5,116,315 A | 5/1992 | Capozzi et al. |
| 5,120,657 A | 6/1992 | McCabe et al. |
| 5,129,825 A | 7/1992 | Discko, Jr. |
| 5,129,882 A | 7/1992 | Weldon et al. |
| 5,133,701 A | 7/1992 | Han |
| 5,135,484 A | 8/1992 | Wright |
| 5,141,515 A | 8/1992 | Eberbach |
| 5,147,292 A | 9/1992 | Kullas et al. |
| 5,149,655 A | 9/1992 | McCabe et al. |
| 5,165,604 A | 11/1992 | Copp, Jr. |
| 5,176,642 A | 1/1993 | Clement |
| 5,179,022 A | 1/1993 | Sanford et al. |
| D333,000 S | 2/1993 | Good et al. |
| 5,204,253 A | 4/1993 | Sanford et al. |
| 5,207,641 A * | 5/1993 | Allton .............. A61M 16/0463 604/32 |
| 5,219,328 A | 6/1993 | Morse et al. |
| 5,226,567 A | 7/1993 | Sansalone |
| 5,226,877 A | 7/1993 | Epstein |
| RE34,365 E | 8/1993 | Theeuwes |
| 5,273,531 A | 12/1993 | Knoepfler |
| 5,292,309 A | 3/1994 | Van Tassel et al. |
| 5,310,407 A | 5/1994 | Casale |
| 5,312,331 A | 5/1994 | Knoepfler |
| 5,312,333 A | 5/1994 | Churinetz et al. |
| 5,328,459 A | 7/1994 | Laghi |
| 5,330,426 A | 7/1994 | Kriesel et al. |
| 5,337,740 A | 8/1994 | Armstrong et al. |

(56) References Cited

U.S. PATENT DOCUMENTS

| | | |
|---|---|---|
| 5,391,183 A | 2/1995 | Janzen et al. |
| 5,392,992 A | 2/1995 | Farnsteiner et al. |
| 5,395,326 A | 3/1995 | Haber et al. |
| 5,405,607 A | 4/1995 | Epstein |
| 5,415,631 A | 5/1995 | Churinetz et al. |
| 5,429,278 A | 7/1995 | Sansalore |
| 5,445,512 A | 8/1995 | Terakura et al. |
| 5,445,612 A | 8/1995 | Terakura et al. |
| 5,447,499 A | 9/1995 | Allaire et al. |
| 5,469,994 A | 11/1995 | Reh et al. |
| 5,470,311 A | 11/1995 | Setterstrom et al. |
| 5,484,403 A | 1/1996 | Yaokum et al. |
| 5,497,232 A | 3/1996 | Watano et al. |
| 5,503,623 A | 4/1996 | Tilton, Jr. |
| 5,513,630 A | 5/1996 | Century |
| 5,518,546 A | 5/1996 | Williams et al. |
| 5,520,658 A | 5/1996 | Holm |
| 5,520,667 A | 5/1996 | Roche |
| 5,538,162 A | 7/1996 | Reh et al. |
| 5,546,932 A | 8/1996 | Galli |
| 5,553,741 A | 9/1996 | Sancoff et al. |
| 5,558,646 A | 9/1996 | Roche |
| 5,582,596 A | 12/1996 | Fukunaga et al. |
| 5,584,807 A | 12/1996 | McCabe |
| 5,584,815 A | 12/1996 | Pawelka et al. |
| 5,601,603 A | 2/1997 | Illi |
| 5,605,541 A | 2/1997 | Holm |
| 5,612,050 A | 3/1997 | Rowe et al. |
| 5,665,067 A | 9/1997 | Linder et al. |
| 5,697,947 A | 12/1997 | Wolf et al. |
| 5,707,402 A | 1/1998 | Heim |
| 5,749,968 A | 5/1998 | Melanson et al. |
| 5,759,171 A | 6/1998 | Coelho |
| 5,788,625 A | 8/1998 | Plouhar et al. |
| 5,865,796 A | 2/1999 | McCabe |
| 5,873,530 A | 2/1999 | Chizinsky |
| 5,882,332 A | 3/1999 | Wijay |
| 5,895,400 A | 4/1999 | Abela |
| 5,902,228 A | 5/1999 | Schulsinger et al. |
| 5,919,184 A | 7/1999 | Tilton, Jr. |
| 5,951,531 A | 9/1999 | Ferdman et al. |
| 6,007,515 A | 12/1999 | Epstein et al. |
| 6,013,050 A | 1/2000 | Bellhouse et al. |
| 6,021,776 A | 2/2000 | Allred et al. |
| 6,027,471 A | 2/2000 | Fallon et al. |
| 6,059,749 A | 5/2000 | Marx |
| 6,077,217 A | 6/2000 | Love et al. |
| 6,117,150 A | 9/2000 | Pingleton et al. |
| 6,123,070 A | 9/2000 | Bruna |
| 6,158,624 A | 12/2000 | Grigg et al. |
| 6,165,201 A | 12/2000 | Sawhney et al. |
| 6,368,300 B1 | 4/2002 | Fallon et al. |
| 6,394,975 B1 | 5/2002 | Epstein |
| 6,428,505 B1 | 8/2002 | Taylor et al. |
| 6,454,786 B1 | 9/2002 | Holm et al. |
| 6,461,325 B1 | 10/2002 | Delmotte et al. |
| 6,461,361 B1 | 10/2002 | Epstein |
| 6,478,754 B1 | 11/2002 | Babeav |
| 6,554,792 B2 | 4/2003 | Hughes et al. |
| 6,537,246 B1 | 5/2003 | Unger et al. |
| 6,610,026 B2 | 8/2003 | Cragg et al. |
| 6,616,652 B1 | 9/2003 | Harper |
| 6,641,800 B1 | 11/2003 | Mistry et al. |
| 6,689,108 B2 | 2/2004 | Lavi et al. |
| 6,716,190 B1 | 4/2004 | Glines et al. |
| 6,723,067 B2 | 4/2004 | Nielson |
| 6,811,550 B2 | 11/2004 | Holland et al. |
| 6,843,388 B1 | 1/2005 | Hollars |
| 6,863,660 B2 | 3/2005 | Marx |
| 6,905,475 B2 | 6/2005 | Hauschild et al. |
| 6,913,596 B2 | 7/2005 | Davey |
| 6,939,324 B2 | 9/2005 | Gonnelli et al. |
| 7,101,862 B2 | 9/2006 | Chochrum et al. |
| 7,156,880 B2 | 1/2007 | Evans et al. |
| 7,178,744 B2 | 2/2007 | Tapphorn et al. |
| 7,182,748 B1 | 2/2007 | Potter et al. |
| 7,291,133 B1 | 6/2007 | Kindler et al. |
| 7,334,598 B1 | 2/2008 | Hollars |
| 7,455,248 B2 | 11/2008 | Kablik et al. |
| 7,534,449 B2 | 5/2009 | Saltzman et al. |
| 7,544,177 B2 | 6/2009 | Gertner |
| 7,547,292 B2 | 6/2009 | Sheldrake et al. |
| 7,588,171 B2 | 9/2009 | Reedy et al. |
| 7,632,245 B1 | 12/2009 | Cowan et al. |
| 7,648,083 B2 | 1/2010 | Hornsby et al. |
| 7,673,783 B2 | 3/2010 | Morgan et al. |
| 7,691,244 B2 | 4/2010 | Levitan et al. |
| 7,744,526 B2 | 6/2010 | McAlister et al. |
| 7,776,822 B2 | 8/2010 | Terman |
| 7,824,373 B2 | 11/2010 | Kim |
| 7,857,167 B1 | 12/2010 | Hollars |
| 7,914,517 B2 | 3/2011 | Baran et al. |
| 8,083,721 B2 | 12/2011 | Miller |
| 8,109,872 B2 | 2/2012 | Kennedy, II et al. |
| 8,118,772 B2 | 2/2012 | Ducharme |
| 8,118,777 B2 | 2/2012 | Ducharme et al. |
| 8,210,449 B2 | 7/2012 | Peterson et al. |
| 8,235,937 B2 | 8/2012 | Palasis et al. |
| 8,292,197 B2 | 10/2012 | Ballu et al. |
| 8,298,175 B2 | 10/2012 | Hirschel et al. |
| RE43,824 E | 11/2012 | Sheldrake et al. |
| 8,361,054 B2 | 1/2013 | Ducharme et al. |
| 8,372,092 B2 | 2/2013 | Gabel et al. |
| 8,418,775 B2 | 4/2013 | Blomet et al. |
| 8,523,821 B2 | 9/2013 | Miller |
| 8,721,582 B2 | 5/2014 | Ji |
| 8,728,032 B2 | 5/2014 | Ducharme et al. |
| 8,827,980 B2 | 9/2014 | Ji |
| 8,944,926 B2 | 2/2015 | Vogt et al. |
| 8,950,396 B2 | 2/2015 | Wachtel et al. |
| 9,101,744 B2 | 8/2015 | Ducharme |
| 9,205,207 B2 | 12/2015 | Ji |
| 9,205,240 B2 | 12/2015 | Greenhalgh et al. |
| 9,375,533 B2 | 6/2016 | Ducharme et al. |
| 9,393,583 B2 | 7/2016 | Tu |
| 9,474,915 B2 | 10/2016 | Gonzales et al. |
| 9,486,609 B2 | 11/2016 | Ross |
| 9,555,185 B2 | 1/2017 | Foster et al. |
| 9,629,966 B2 | 4/2017 | Ji |
| 9,837,931 B2 | 12/2017 | Luo |
| 9,839,772 B2 | 12/2017 | Ducharme |
| 9,867,931 B2 | 1/2018 | Gittard |
| 9,895,527 B2 | 2/2018 | Spohn et al. |
| 9,907,456 B2 | 3/2018 | Miyioshi |
| 10,463,811 B2 | 11/2019 | Lee et al. |
| 10,542,868 B2 | 1/2020 | Gordon et al. |
| 10,610,665 B2 | 4/2020 | Krueger et al. |
| 10,806,853 B2 | 10/2020 | Gittard |
| 10,842,368 B2 | 11/2020 | Nave |
| 10,994,110 B2 | 5/2021 | Ducharme |
| 11,344,314 B2 | 5/2022 | Tal et al. |
| 11,766,546 B2 | 9/2023 | Pic et al. |
| 2001/0056256 A1 | 12/2001 | Hughes et al. |
| 2002/0165483 A1 | 11/2002 | Miller |
| 2002/0169416 A1 | 11/2002 | Gonnelli |
| 2003/0023202 A1 | 1/2003 | Nielson et al. |
| 2003/0032862 A1 | 2/2003 | Ota et al. |
| 2003/0069549 A1* | 4/2003 | MacMahon ............. A61M 1/67 604/266 |
| 2003/0108511 A1 | 6/2003 | Sawhney |
| 2003/0170250 A1 | 9/2003 | Ezrin et al. |
| 2003/0181917 A1 | 9/2003 | Gertner |
| 2003/0216695 A1 | 11/2003 | Yang |
| 2004/0059283 A1 | 3/2004 | Kirwan et al. |
| 2004/0073863 A1 | 4/2004 | Mousley |
| 2004/0215135 A1 | 10/2004 | Sheldrake et al. |
| 2004/0262340 A1 | 12/2004 | Kress |
| 2005/0070848 A1 | 3/2005 | Kim et al. |
| 2005/0125002 A1 | 6/2005 | Baran et al. |
| 2005/0205087 A1 | 9/2005 | Kablik et al. |
| 2006/0002852 A1 | 1/2006 | Saltzman et al. |
| 2006/0052295 A1 | 3/2006 | Terman |
| 2006/0100572 A1 | 5/2006 | DiMatteo et al. |

(56) References Cited

U.S. PATENT DOCUMENTS

| | | | |
|---|---|---|---|
| 2006/0252993 A1* | 11/2006 | Freed | A61B 1/0052 |
| | | | 604/95.04 |
| 2006/0028664 A1 | 12/2006 | McAllister et al. | |
| 2007/0005002 A1* | 1/2007 | Millman | A61B 34/71 |
| | | | 604/30 |
| 2007/0088317 A1 | 4/2007 | Hyde | |
| 2007/0199824 A1 | 8/2007 | Hoerr et al. | |
| 2007/0240989 A1 | 10/2007 | Levitan et al. | |
| 2007/0241119 A1 | 10/2007 | Durkin et al. | |
| 2008/0021374 A1 | 1/2008 | Kawata | |
| 2008/0027272 A1 | 1/2008 | Kadykowski | |
| 2008/0120992 A1 | 5/2008 | Levy et al. | |
| 2008/0132891 A1 | 6/2008 | Nobis et al. | |
| 2008/0287911 A1 | 11/2008 | El-Nounou et al. | |
| 2009/0000615 A1 | 1/2009 | Pohlmann | |
| 2009/0007904 A1 | 1/2009 | Schuster et al. | |
| 2009/0030274 A1 | 1/2009 | Goldfarb et al. | |
| 2009/0071470 A1 | 3/2009 | Abrams | |
| 2009/0145982 A1 | 6/2009 | Blomet et al. | |
| 2009/0155342 A1 | 6/2009 | Diegelmann et al. | |
| 2009/0234227 A1* | 9/2009 | Punga | A61F 2/95 |
| | | | 604/264 |
| 2009/0234374 A1 | 9/2009 | Gabel et al. | |
| 2009/0234380 A1 | 9/2009 | Gabel et al. | |
| 2009/0240197 A1 | 9/2009 | Cowan et al. | |
| 2009/0248056 A1 | 10/2009 | Gabel et al. | |
| 2009/0281486 A1 | 11/2009 | Ducharme | |
| 2009/0326453 A1 | 12/2009 | Adams et al. | |
| 2010/0101579 A1 | 4/2010 | Levy | |
| 2010/0121261 A1 | 5/2010 | Kablik et al. | |
| 2010/0137796 A1 | 6/2010 | Perry et al. | |
| 2010/0160897 A1 | 6/2010 | Ducharme et al. | |
| 2010/0191185 A1 | 7/2010 | Miller | |
| 2010/0305505 A1 | 12/2010 | Ducharme et al. | |
| 2011/0178495 A1 | 7/2011 | Ji | |
| 2011/0272438 A1 | 11/2011 | Vogt et al. | |
| 2012/0116296 A1 | 5/2012 | Ducharme et al. | |
| 2012/0136301 A1 | 5/2012 | Miller | |
| 2013/0046278 A1 | 2/2013 | Ji | |
| 2013/0059113 A1 | 3/2013 | Hatton et al. | |
| 2013/0100801 A1 | 4/2013 | Allan et al. | |
| 2013/0104884 A1 | 5/2013 | Vazales et al. | |
| 2013/0110080 A1* | 5/2013 | Ducharme | A61M 5/155 |
| | | | 604/506 |
| 2014/0200402 A1* | 7/2014 | Snoke | A61B 1/00121 |
| | | | 600/104 |
| 2014/0207097 A1 | 7/2014 | Ji | |
| 2014/0248437 A1 | 9/2014 | Schroeder et al. | |
| 2014/0271491 A1 | 9/2014 | Gittard et al. | |
| 2014/0296806 A1 | 10/2014 | Williams et al. | |
| 2014/0346257 A1 | 11/2014 | Reetz, III et al. | |
| 2015/0216516 A1 | 8/2015 | Steffen | |
| 2015/0306317 A1 | 10/2015 | Ducharme et al. | |
| 2017/0224762 A1 | 8/2017 | McIntosh et al. | |
| 2017/0232141 A1 | 8/2017 | Surti et al. | |
| 2017/0265879 A1 | 9/2017 | Washburn, II et al. | |
| 2017/0296221 A1 | 10/2017 | DiCaprio et al. | |
| 2018/0001067 A1 | 1/2018 | Christakis et al. | |
| 2018/0056052 A1 | 3/2018 | Swanson et al. | |
| 2018/0099088 A1 | 4/2018 | Gittard | |
| 2018/0161526 A1 | 6/2018 | Canner et al. | |
| 2018/0193011 A1 | 7/2018 | Keene et al. | |
| 2018/0193574 A1 | 7/2018 | Smith et al. | |
| 2018/0221296 A1 | 8/2018 | Holekamp et al. | |
| 2018/0344659 A1 | 12/2018 | Holekamp et al. | |
| 2019/0008601 A1 | 1/2019 | Pereira et al. | |
| 2019/0232030 A1 | 8/2019 | Pic et al. | |
| 2019/0308213 A1 | 10/2019 | Mispel-Beyer | |
| 2019/0322442 A1 | 10/2019 | Thomsen | |
| 2019/0343980 A1 | 11/2019 | Gittard et al. | |
| 2019/0351207 A1 | 11/2019 | Quan et al. | |
| 2019/0388665 A1 | 12/2019 | Christakis et al. | |
| 2020/0046213 A1 | 2/2020 | Bendory et al. | |
| 2020/0060536 A1 | 2/2020 | Rylander et al. | |
| 2020/0061310 A1 | 2/2020 | Goodman et al. | |
| 2020/0100986 A1 | 4/2020 | Pic et al. | |
| 2020/0101476 A1 | 4/2020 | Pic et al. | |
| 2020/0222218 A1 | 7/2020 | Poulsen et al. | |
| 2020/0397983 A1 | 12/2020 | Gittard | |
| 2021/0022761 A1 | 1/2021 | Looper et al. | |
| 2021/0106717 A1 | 4/2021 | Carruthers et al. | |
| 2021/0161515 A1 | 6/2021 | Pic et al. | |
| 2021/0162122 A1 | 6/2021 | Pic et al. | |
| 2021/0187190 A1 | 6/2021 | Congdon et al. | |
| 2021/0228852 A1 | 7/2021 | Ducharme | |
| 2021/0275760 A1 | 9/2021 | Hunter et al. | |
| 2021/0299400 A1 | 9/2021 | Cauche et al. | |
| 2021/0346568 A1 | 11/2021 | Gittard et al. | |
| 2021/0379302 A1 | 12/2021 | Sigmon et al. | |
| 2022/0040006 A1 | 2/2022 | Surti et al. | |
| 2023/0016512 A1 | 1/2023 | Slattery et al. | |
| 2023/0390540 A1 | 12/2023 | Pic et al. | |

FOREIGN PATENT DOCUMENTS

| | | |
|---|---|---|
| AU | 2009330505 | 6/2011 |
| AU | 2011202035 | 11/2011 |
| AU | 2010253997 | 12/2011 |
| AU | 2014237970 | 9/2015 |
| AU | 2014329827 | 4/2016 |
| BR | 112022023464.3 | 12/2022 |
| CA | 2194096 | 8/2005 |
| CA | 2723183 | 11/2009 |
| CA | 2747390 | 7/2010 |
| CA | 2751538 | 8/2010 |
| CA | 2763135 | 12/2010 |
| CA | 2585845 | 12/2012 |
| CA | 2925900 | 4/2015 |
| CA | 2737832 | 2/2016 |
| CH | 15244 A | 9/1897 |
| CH | 257250 A | 3/1949 |
| CN | 101068555 A | 11/2007 |
| CN | 101820935 A | 9/2010 |
| CN | 105050630 A | 11/2015 |
| CN | 105792869 A | 7/2016 |
| CN | 201621061301.6 | 9/2016 |
| CN | 201820339550.X | 3/2018 |
| CN | 110691615 A | 1/2020 |
| CN | 112546336 A | 3/2021 |
| CN | 113080819 A | 7/2021 |
| CN | 114514017 A | 5/2022 |
| CN | 115697176 A | 2/2023 |
| DE | 3024749 A1 | 2/1982 |
| DE | 3108918 A1 | 9/1982 |
| DE | 3613762 A1 | 11/1987 |
| DE | 69529495 | 3/2003 |
| DE | 69530843 | 6/2003 |
| DE | 10 2004 011 444 A1 | 9/2005 |
| DE | 60210063 | 5/2006 |
| DE | 602005005081 | 4/2008 |
| DE | 102010019222 | 11/2013 |
| EP | 308269 A1 | 3/1989 |
| EP | 0 692 273 | 1/1996 |
| EP | 0738498 A1 | 10/1996 |
| EP | 0690732 | 1/2003 |
| EP | 0767624 | 5/2003 |
| EP | 1293559 | 7/2005 |
| EP | 1550713 | 7/2005 |
| EP | 1365824 B1 | 3/2006 |
| EP | 1804926 | 2/2008 |
| EP | 2277577 | 1/2011 |
| EP | 2384871 | 11/2011 |
| EP | 2391411 | 12/2011 |
| EP | 2435114 | 4/2012 |
| EP | 2680912 | 8/2015 |
| EP | 2934629 | 10/2015 |
| EP | 2968651 | 1/2016 |
| EP | 3150240 | 5/2017 |
| EP | 2375960 | 10/2018 |
| EP | 3052168 | 11/2019 |
| EP | 3190981 | 11/2019 |
| EP | 3615094 | 3/2020 |
| EP | 4041196 | 8/2022 |

(56) References Cited

FOREIGN PATENT DOCUMENTS

| | | |
|---|---|---|
| EP | 4161346 | 4/2023 |
| FR | 2863503 | 12/2003 |
| FR | 2877240 | 1/2007 |
| GB | 10563 A | 12/1896 |
| GB | 1254534 A | 11/1971 |
| GB | 2300371 A | 11/1996 |
| GB | 0100756 | 3/2001 |
| JP | S4838435 U | 5/1973 |
| JP | S5667464 U | 6/1981 |
| JP | 4022109 B | 4/1992 |
| JP | 5-192404 | 8/1993 |
| JP | H08206229 | 8/1996 |
| JP | 1997-253032 | 9/1997 |
| JP | 10505253 | 5/1998 |
| JP | 10-508790 | 9/1998 |
| JP | 2001-520918 | 11/2001 |
| JP | 2002-028224 | 1/2002 |
| JP | 2003/024833 A | 1/2003 |
| JP | 2003-126026 | 5/2003 |
| JP | 2004/521677 | 7/2004 |
| JP | 2004-535246 | 11/2004 |
| JP | 2005270372 | 6/2005 |
| JP | 3719608 | 11/2005 |
| JP | 2007-529280 A | 10/2007 |
| JP | 2009-530051 | 8/2009 |
| JP | 2011/508588 | 3/2011 |
| JP | 2011-519679 A | 7/2011 |
| JP | 2011/235962 | 11/2011 |
| JP | 2012-513284 A | 6/2012 |
| JP | 2012-527974 | 11/2012 |
| JP | 5502801 | 5/2014 |
| JP | 5631332 | 11/2014 |
| JP | 5670439 | 12/2014 |
| JP | 2016/512069 A | 4/2016 |
| JP | 6047546 | 11/2016 |
| JP | 6552115 | 7/2019 |
| JP | 2020/517399 | 6/2020 |
| JP | 6715274 B2 | 7/2020 |
| JP | 6807742 | 12/2020 |
| JP | 2020 023110 | 2/2022 |
| JP | 2022/521497 A | 4/2022 |
| JP | 2022/551509 | 9/2022 |
| KR | 102387327 | 4/2022 |
| KR | 10-2023-0002873 | 5/2023 |
| SU | 978999 | 12/1982 |
| TW | 1719844 B | 2/2021 |
| WO | WO 1982/03545 | 10/1982 |
| WO | WO2008/023545 | 10/1982 |
| WO | WO1985/002346 | 6/1985 |
| WO | WO1992/020312 | 11/1992 |
| WO | WO1994/028798 | 12/1994 |
| WO | WO 1995/19799 | 7/1995 |
| WO | WO 1996/009085 | 3/1996 |
| WO | WO 1996/025190 | 8/1996 |
| WO | WO 1996/00524 | 11/1996 |
| WO | WO1996/037245 | 11/1996 |
| WO | WO1996/040327 | 12/1996 |
| WO | WO1997/020585 | 6/1997 |
| WO | WO 1999/12595 | 3/1999 |
| WO | WO 1999/21599 | 5/1999 |
| WO | WO 02/055139 | 7/2002 |
| WO | WO2002/053014 | 7/2002 |
| WO | WO 2003/007797 A1 | 1/2003 |
| WO | WO2004/002551 | 1/2004 |
| WO | WO2004/073863 | 9/2004 |
| WO | WO2005/089472 | 9/2005 |
| WO | WO2005/100980 | 10/2005 |
| WO | WO 2006/048536 | 5/2006 |
| WO | WO 20006/090149 | 8/2006 |
| WO | WO 2007/112185 A1 | 10/2007 |
| WO | WO2008/008845 | 1/2008 |
| WO | WO 2009/088576 | 7/2009 |
| WO | WO2009/091549 | 7/2009 |
| WO | WO 2009/137438 | 11/2009 |
| WO | WO 2010//074949 | 7/2010 |
| WO | WO 2010/088146 | 8/2010 |
| WO | WO 2010/138703 | 12/2010 |
| WO | WO 2012/118466 | 9/2012 |
| WO | WO2013/093798 | 6/2013 |
| WO | WO 2014/099662 | 6/2014 |
| WO | WO 2014/149617 | 9/2014 |
| WO | WO2015/050814 | 4/2015 |
| WO | WO 2016/038593 A1 | 3/2016 |
| WO | WO 2016/111373 | 7/2016 |
| WO | WO 2017/006684 | 1/2017 |
| WO | WO 2017/028701 A1 | 2/2017 |
| WO | WO 2018/200695 | 1/2018 |
| WO | WO 2020/254447 | 12/2020 |
| WO | WO 2021/071751 | 4/2021 |
| WO | WO 2021/141791 A1 | 7/2021 |
| WO | WO 2021/247850 | 12/2021 |
| WO | WO 2023/287654 | 1/2023 |
| WO | WO 2023/076076 A1 | 5/2023 |

OTHER PUBLICATIONS

Communication and Written Opinion dated Jan. 13, 2023 in European Application No. 21736099.9 (14 pages).
International Search Report and Written Opinion of the International Searching Authority dated Dec. 3, 2021 in International Application No. PCT/US2021/035682 (22 pages).
First Office Action and English Translation in Chinese Application No. 2018800357848, dated Jun. 9, 2021 (9 pages).
Response to First Office Action in Chinese Application No. 2018800357848, dated Sep. 17, 2021 (12 pages).
Second Office Action and English Translation in Chinese Application No. 2018800357848, dated Dec. 1, 2021 (8 pages).
Response to Second Office Action in Chinese Application No. 2018800357848, dated March 29, 2022 (9 pages).
Third Office Action and English Translation in Chinese Application No. 2018800357848, dated Mar. 29, 2022 (9 pages).
Response to Examination Report in European Application No. 18724076.7, dated Feb. 25, 2022 (12 pages).
Written Submissions in European Application No. 14789657.5 filed Jan. 7, 2022 (51 pages).
Opponent's Written Submissions in European Application No. 14789657.5 filed Jan. 18, 2022 (25 pages).
First Office Action in Chinese Patent Application No. 2020111614040 dated Mar. 21, 2022 (15 pages).
Cardinal IP Services, "Prevention of Spray Activation During System Closure" (DN-9175) Patentability Search of Disclosure, 13 pages, dated Sep. 30, 2020.
Cardinal IP Services, "Water Ingress Prevention Via Positive (Active/Passive) Air Flow" (DN-9171 and DN-9184) Patentability Search of Disclosure, 15 pages, dated Jan. 13, 2021.
Cardinal IP Services, "Preventing Accidental Powder Deployment" (DN-9387) Patentability Search of Disclosure, 9 pages, dated Nov. 9, 2021.
Cardinal IP Services, "Positive Pressure Delivery Mechanism for a Therapeutic Agent Delivery Device" (DN-9347) Patentability Search of Disclosure, 13 pages, dated Oct. 12, 2021.
Cardinal IP Services, "Catheter Distal End Features to Prevent Lens Irrigation Fluid Ingress" (DN-9378) Patentability Search of Disclosure, 16 pages, dated Nov. 5, 2021.
Cardinal IP Services, "Device That Allows For Cleaning of Catheter and Camera Lens on Endoscope Distal Tip" (DN-9495) Patentability Search of Disclosure, 11 pages, dated Jan. 3, 2022.
PCT International Search Report in related Application No. PCT/US2022/036498 dated Oct. 27, 2022 (15 pages).
Cook Hemospray Set-Up Video. Describes Turning of Valve to Allow for Trigger to Function; Retrieved from https://www.cookmedical.com/products/35a4a7f2-867b-4081-a933-44ea06277852/, dated 2020.
Patentability Search: "Review of Cook's Hemostatic and Mucoadhesive Patents" dated Feb. 14, 2023 (32 pages).
Patentability Search of Disclosure Entitled "Device That Reduces Fluid Ingress in the Catheter" (DN-9596) Prepared by Cardinal IP Services, dated Aug. 24, 2022 (12 pages).

(56) References Cited

OTHER PUBLICATIONS

Invitation to Pay Additional Fee and, Where Applicable, Protest Fee in PCT Application Serial No. PCT/US2022/047013, dated Feb. 6, 2023 (13 pages).
International Preliminary Report on Patentability in PCT Application No. PCT/US/2021/035682, dated Dec. 6, 2022 (13 pages).
International Search Report and The Written Opinion of the International Searching Authority in PCT Application Serial No. PCT/US2022/047013, dated Mar. 27, 2023 (20 pages).
Office Action dated Aug. 4, 2010 for U.S. Appl. No. 12/435,574, 7 pgs.
Response to Office Action for U.S. Appl. No. 12/435,574, filed Nov. 3, 2010, 10 pgs.
Office Action dated Feb. 17, 2011 for U.S. Appl. No. 12/435,574, 8 pgs.
Response to Office Action for U.S. Appl. No. 12/435,574, filed May 13, 2011, 11 pgs.
Office Action dated Aug. 22, 2011 for U.S. Appl. No. 12/435,574, 9 pgs.
Response to Office Action for U.S. Appl. No. 12/435,574 filed Nov. 22, 2011, 10 pgs.
Office Action dated Mar. 30, 2012 for U.S. Appl. No. 12/435,574, 9 pgs.
Response to Office Action for U.S. Appl. No. 12/435,574 filed Aug. 30, 2012, 11 pgs.
Restriction Requirement dated May 25, 2012 for U.S. Appl. No. 12/633,027, 7 pgs.
Response to Restriction Requirement filed Jul. 2, 2012 for U.S. Appl. No. 12/633,027, 7 pgs.
Office Action dated Apr. 14, 2011 for U.S. Appl. No. 12/787,796, 9 pgs.
Response to Office Action filed Jul. 14, 2011 for U.S. Appl. No. 12/787,796, 11 pgs.
Notice of Allowance dated Oct. 18, 2011 for U.S. Appl. No. 12/787,796, 10 pgs.
International Search Report and Written Opinion for PCT/US2009/067076, mailed Apr. 14, 2010, 23 pgs.
International Search Report and Written Opinion for PCT/US2010/036381, mailed Aug. 20, 2010, 16 pgs.
International Preliminary Report on Patentability for PCT/US2009/042781, mailed Nov. 18, 2010, 10 pgs.
International Search Report completed Sep. 22, 2009 for PCT/US2009/042781, 7 pgs.
Alto Shooter Catalog, Kaigen, English and Japanese, Jun. 1994, 8 pgs.
Decker, "An Efficient Method For The Application Of Avitene Hemostatic Agent", Surgeg, Gynecology & Obstetrics, 1991, vol. 172, No. 6, 2 pgs.
Endo-Avitene™ Brochure "Microfibrillar Collagen Hemostat in an Endoscopic Delivery System", from MedChem Products, 4 pgs, 1992.
Fagelman, et al. "A Simple Method For Application Of Microfibrilar Colagen", Surgery, Gynecology & Obstetrics, Jun. 1980, vol. 150, No. 6, 3 pgs.
Hoshino, et al. "Trans-endoscopic Drug Propulsion Therapy", Diagnostic Endoscopy, 1993, vol. 5, 6 pgs.
Surgical Armamentarium, Copyright 1973 V. Mueller, 3 pgs.
Hoshino, "Transendoscopic Projectile Drug Delivery", Gastroenterologia Japonica, vol. 25, No. 5, Jun. 15, 1990, 1 page.
Park et al., "A randomized comparison of a new flexible bipolar hemostasis forceps designed principally for NOTES versus a conventional surgical laparoscopic bipolar forceps for intra-abdominal vessel sealing in a porcine model", Gastrointestinal Endoscopy 2010, vol. 71, No. 4, pp. 835-841.
Fritscher-Ravens et al., "Beyond NOTES: randomized controlled study of different methods of flexible endoscopic hemostasis of artifically induced hemorrhage, via NOTES access to the Beritoneal cavity", Endoscopy 2009, vol. 41, pp. 29-35.
Final Office Action for U.S. Appl. No. 12/435,574 mailed Feb. 17, 2011, 8 pgs.
Examiner Interview Summary for U.S. Appl. No. 12/435,574 dated Jun. 10, 2011, 3 pgs.
Notice of Appeal for U.S. Appl. No. 12/435,574 filed Aug. 17, 2011, 1 pg.
Notice of Allowance dated Oct. 5, 2012 for U.S. Appl. No. 12/633,027, 9 pgs.
International Preliminary Report on Patentability for PCT/US2009/067076 issued Jun. 29, 2011, 12 pgs.
International Preliminary Report on Patentability for PCT/US2010/036381 issued Nov. 29, 2011, 7 pgs.
Examination Report for Australian Patent Application No. 2009244462 issued Sep. 27, 2012; 4 pgs.
Response to Examination Report for Australian Patent Application No. 2009244462 filed Feb. 19, 2013; 8 pgs.
Examination Report for Canadian Patent Application No. 2,723,183 issued Aug. 17, 2012, 2 pgs.
Response to Examination Report for Canadian Patent Application No. 2,723,183 filed Feb. 11, 2013, 5 pgs.
Examination Report for European Patent Application No. 09743424.5 issued Nov. 14, 2011, 5 pgs.
Response to Examination Report for European Patent Application No. 09743424.5 filed Mar. 14, 2012, 10 pgs.
Examination Report for European Patent Application No. 09743424.5 issued Sep. 5, 2012, 6 pgs.
Response to Examination Report for European Patent Application No. 09743424.5 filed Feb. 22, 2013, 4 pgs.
Office Action for U.S. Appl. No. 13/351,524 issued Oct. 18, 2012, 14 pgs.
Examiner Interview Summary for U.S. Appl. No. 13/351,524 issued Feb. 8, 2013, 4 pgs.
Response to Office Action for U.S. Appl. No. 13/351,524 filed Feb. 12, 2013, 9 pgs.
First Australian Examination Report for related AU Application No. 2014329827, dated Aug. 29, 2016, 4 pgs.
Reply to First Australian Examination Report for related AU Application No. 2014329827, dated Nov. 10, 2016, 16 pgs.
Notice of Acceptance For Patent Application for related AU Application No. 2014329827, dated Dec. 12, 2016, 3 pgs.
Canadian Examination Report for related CA Application No. 2,925,900, dated Feb. 23, 2017, 4 pgs.
European Communication Pursuant to Rule 161 (1) and 162 for related EP Application No. 14789657.5, dated May 11, 2016, 2 pgs.
Reply To European Communication Report dated Nov. 10, 2016, 8 pgs.
PCT International Search Report and Written Opinion for related Application No. PCT/US2014/058016, dated Apr. 21, 2015, 15 pgs.
Office Action for JP2016-520011 dated May 2, 2017, 7 pgs. Including English translation.
John Chadwick, Particle Size Control in Aerosol Packages, Dec. 2004, Aerosol Technical Solutions, pp. 1-3.
Response to Examiner's Report in Canadian Application No. 2,925,900, dated Aug. 23, 2017, 6 pages.
Notice of Allowance in Canadian Application No. 2,925,900, dated Dec. 1, 2017, 1 page.
Office Action/Notification of Reason for Rejection in Japanese Application No. 2016-520011 dated Apr. 24, 2018, including English translation, 7 pages.
Office Action in Chinese Application No. 201480065570.7 dated Jun. 22, 2018, including English translation, 21 pages.
Response to Office Action for Chinese Application No. 201480065570.7 filed Oct. 5, 2018, including English translation, 6 pgs.
Response to Office Action for Canadian Application No. 2,925,900 filed Aug. 23, 2017, 32 pgs.
Response to Office Action for Japanese Application No. 2016-520011 filed Nov. 1, 2017, 11 pgs.
Response to Office Action for Japanese Application No. 2016-520011 filed Oct. 23, 2018, 3 pgs.
Office Action for EP 13818576.4 issued Oct. 9, 2018, 6 pgs.
Second Office Action for CN201480065570.7 dated Mar. 11, 2019, 7 pages.
Office Action for Japanese Patent Application 2016-520011 dated Apr. 2, 2019, 5 pgs. including English translation.

(56) References Cited

OTHER PUBLICATIONS

Response to Office Action for Japanese Patent Application 2014-80065570.7 filed May 22, 2019, 11 pgs.
Intent to Grant for European Application 14 789 657.5 dated Jun. 17, 2019, 35 pgs.
Third Office Action for Chinese Patent Application No. 201480065570.7 dated Sep. 25, 2019, 14 pgs. including English translation.
Office Action for Japanese Patent Application Serial No. 2016-520011 (Appeal No. 2019-0102252), dated Jun. 24, 2020, 8 pgs; including English translation.
Office Action for Chinese Patent Application filing No. 201480065570.7 dated Apr. 3, 2020, 7 pgs. including English translation.
Notice of Opposition for European Patent Application No. 14789657.5 dated Aug. 26, 2020, 28 pgs.
ASTM, "ASTM E2651-10, Standard Guide for Powder Particle Size Analysis", West Conshohocken, PA, USA: ASTM International, 2010.
Muzzio, F.J. et al., "Sampling and characterization of pharmaceutical powders and granular blends", International Journal of Pharmaceutics, vol. 250, No. 51-64, 2003.
Kuchling, H., "Taschenbuch der Physik", Fachbuchverlag Leipzig GmbH, 1995, Ed. 15: pp. 166-169; 9 pages including English translation.
Kibbe, A.H. et al., "Lactose. In: R.C. Rowe et al. (eds). Handbook of Pharmaceutical Excipients", London: Pharmaceutical Press, 2003: pp. 323-332.
National Geographic Area Coordination Center, "'Weed Washer' What is a Micron? (Micron v/s Mesh). Reference: Mesh Micron Conversion Chart", [cited Jun. 8, 2020] Available from: [https://gacc.nifc.gov/nrcc/dispatch/equipment_supplies/agree-contract/forms/M icronMesh.pdf].
Mortazavi, S.M.J., "Development of a Novel Mineral Based Haemostatic Agent Consisting of a Combination of Bentonite and Zeolite Minerals", J Ayub Med Coll Abbottabad, vol. 21(1), 2009.
ChemicalBook Inc., "Chemical Book, CAS DataBase List, Bentonite", CAS No. 1302-78-9 II, [cited Jun. 8, 2020] Available from: [https://www.chemicalbook.com/CASEN_1302-78-9.htm].
Kesavan, J. et al., "Density Measurements of Materials used in Aerosol Studies", Edgewood, 2000.
Arefnia, A. et al., "Comparative Study on the Effect of Tire-Derived Aggregate on Specific Gravity of Kaolin", Electronic Journal of Geotechnical Engineering, vol. 18(B), Jan. 2013: pp. 335-344.
Wikipedia, "Wikipedia. Amoxicillin", [cited Jun. 8, 2020] Available from: [https://en.wikipedia.org/wiki/Amoxicillin].
ChemicalBook Inc., "Chemical Book. Norfloxacin", [cited Jun. 8, 2020] Available from: [https://www.chemicalbook.com/ChemicalProductProperty_US_CB1711035.aspx].
Wong Kee Song, L.-M. et al., "Emerging technologies for endoscopic hemostasis", Gastrointest. Endosc., vol. 75(5), May 2012: pp. 933-937.
Bridevaux, et al. "Short-term safety of thoracoscopic talc pleurodesis for recurrent primary spontaneous pneumothorax; a prospective European multicentre study" Eur Respir J 2011; 38: 770-773. (Year: 2011).
International Preliminary Report on Patentability in PCT Application No. PCT/US/2014/058016, dated Oct. 2, 2013 (12 pages).
Reexamination Request in Chinese Application No. 201480065570.7, dated Jul. 3, 2020 (10 pages).
Notice of Allowance in Chinese Application No. 201480065570.7, dated Aug. 12, 2020 (4 pages).
Response to Office Action in European Application No. 14789657.5, dated Mar. 22, 2021 (85 Pages).
Response to Office Action in Japanese Application No. 2016-520011, dated Sep. 15, 2020 (4 pages).
Decision on Appeal in Japanese Application No. 2016-520011, dated Nov. 10, 2020 (4 pages).
Summons to Attend Oral Proceedings in European Application No. 14789657.5, dated Aug. 26, 2021 (13 pages).
PCT Invitation to Pay Additional Fees in related Application No. PCT/US2021/035682 dated Oct. 12, 2021 (16 pages).
Partial European Search Report in EP Application No. 23214435.2, dated Apr. 23, 2024 (14 pages).
Medgadget, *Convesaid, A Hemostat Powder Spray That Can't Cause Embolisms*, (Team Consulting) Mar. 16, 2018 (4 pages).
Partial European Search Report in EP Application No. 23204400.8, dated Mar. 18, 2024 (17 pages).
International Preliminary Report on Patentability and Written Opinion regarding PCT/US2022/036498 dated Jan. 25, 2024, 9 pages.
Office Action in Japanese Patent Application No. 2022-570158, dated Nov. 17, 2023 (9 pages).
Machine Translation of JP 1997-253032 (21 pages).
International Preliminary Report on Patentability in PCT Application No. PCT/US2022/047013, dated Apr. 30, 2024 (12 pages).
Japanese Decision of Refusal and English translation of the Office Action regarding 2022-570158 dated Jul. 23, 2024, 5 pages.
Office Action for Japanese Patent Application No. 2011-508588 dated Mar. 25, 2014, 6 pages including English translation.
Office Action dated Jun. 12, 2013 for Japanese Patent Application No. 2011-508588, 6 pages inlcluding English translation.
Response to Office Action dated Oct. 10, 2013 for Japanese Patent Application No. 2011-508588, 3 pages.
Examination Report from European Patent Office dated Nov. 28, 2013 for European Patent Application No. 09743424.5, 6 pgs.
Examiner's Report dated Aug. 17, 2012 for Canadian Patent Application No. 2723183, 2 pgs.
Response to Examiner's Report dated Feb. 11, 2013 for Canadian Patent Application No. 2723183, 5 pgs.
Notice of Allowance dated Jul. 31, 2013 for Canadian Patent Application No. 2723183, 1 pg.
Notice of Acceptance dated Apr. 2, 2013 for Australian Patent Application No. 2009244462, 3 pgs.
Certificate of Grant dated Jul. 25, 2013 for Australian Patent Application No. 2009244462, 1 pg.
Office Action dated Oct. 2, 2014 for U.S. Appl. No. 12/435,574, 10 pgs.
Response to Office Action filed Feb. 24, 2015 for U.S. Appl. No. 12/435,574, 18 pgs.
Office Action dated Jun. 12, 2015 for U.S. Appl. No. 12/435,574, 10 pgs.
Response to Office Action filed Oct. 6, 2015 for U.S. Appl. No. 12/435,574, 19 pgs.
Office Action dated dated Jun. 1, 2016 for U.S. Appl. No. 12/435,574, 13 pgs.
Response to Office Action filed Aug. 2, 2016 for U.S. Appl. No. 12/435,574, 13 pgs.
Office Action dated Nov. 15, 2016 for U.S. Appl. No. 12/435,574, 15 pgs.
Notice of Allowance dated Aug. 10, 2017 for U.S. Appl. No. 12/435,572, 9 pgs.
PCT International Search Report and Written Opinion for PCT/US2010/036381, mailed Aug. 20, 2010 (16 pages).
Final Rejection for U.S. Appl. No. 13/351,524 issued Jun. 14, 2013, 12 pgs.
RCE and Amendment for U.S. Appl. No. 13/351,524, filed Dec. 13, 2013, 10 pgs.
Notice of Allowance for U.S. Appl. No. 13/351,524 issued Jan. 17, 2014, 9 pgs.
Examination Report No. 1 for Australian Patent Application 2010253997 issued Mar. 15, 2013, 3 pgs.
Examiner's Report for Canadian Patent Application 2,763,135 issued May 27, 2013, 3 pgs.
Response to Examiner's Report for Canadian Patent Application 2,763,135 filed Nov. 27, 2013, 8 pgs.
Communication for European Patent Application 10722265.5 dated Jan. 27, 2012, 2 pgs.
Reply to Communication for European Patent Application 10722265.5 filed Jul. 27, 2012, 18 pgs.
International Search Report and Written Opinion for PCT/US2013/075005 dated May 2, 2014, 13 pgs.
Office Action dated Oct. 7, 2013 for U.S. Appl. No. 13/725,206, 8 pgs.
Response to Office Action filed Feb. 6, 2014 for U.S. Appl. No. 13/725,206, 8 pgs.

(56) References Cited

OTHER PUBLICATIONS

Office Action dated May 29, 2014 for U.S. Appl. No. 13/725,206, 10 pgs.
Pre-Appeal Brief Request for Review filed Oct. 28, 2014 for U.S. Appl. No. 13/725,206, 7 pgs.
Notice of Panel Decision dated Nov. 25, 2014 for U.S. Appl. No. 13/725,206, 2 pgs.
Amendment and Response After Final filed Jan. 26, 2015 for U.S. Appl. No. 13/725,206, 9 pgs.
Advisory Action dated Feb. 13, 2015 for U.S. Appl. No. 13/725,206, 3 pgs.
Amendment and Response After Final filed Mar. 30, 2015 for U.S. Appl. No. 13/725,206, 8 pgs.
Notice of Allowance dated Apr. 9, 2015 for U.S. Appl. No. 13/725,206, 8 pgs.
Communication Pursuant to Rules 161(1) and 162 EPC for EPO13818576.4 dated Aug. 12, 2015, 2 pgs.
Notification of Reason for Rejection for JP2014-254907 dated Feb. 9, 2016, 6 pgs including English translation.
Office Action in European U.S. Appl. No. 22/802,397 dated Jun. 5, 2024 (23 pages).
Final Office Action in U.S. Appl. No. 17/227,635 dated Aug. 30, 2024 (39 pages).
Final Office Action in U.S. Appl. No. 18/143,844 dated Sep. 4, 2024 (68 pages).
Extended European Search Report in European Application No. 23214435.2, dated Aug. 5, 2024 (14 pages).
Notice of Allowance in U.S. Appl. No. 17/338,198, dated Sep. 9, 2024 (10 pages).

\* cited by examiner

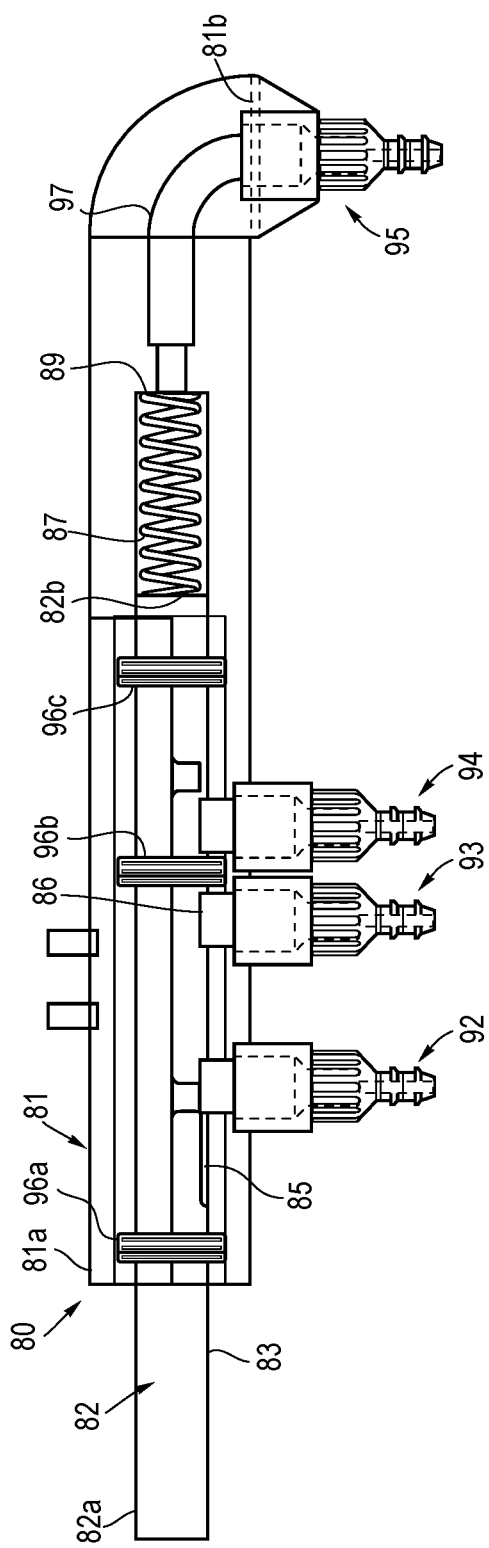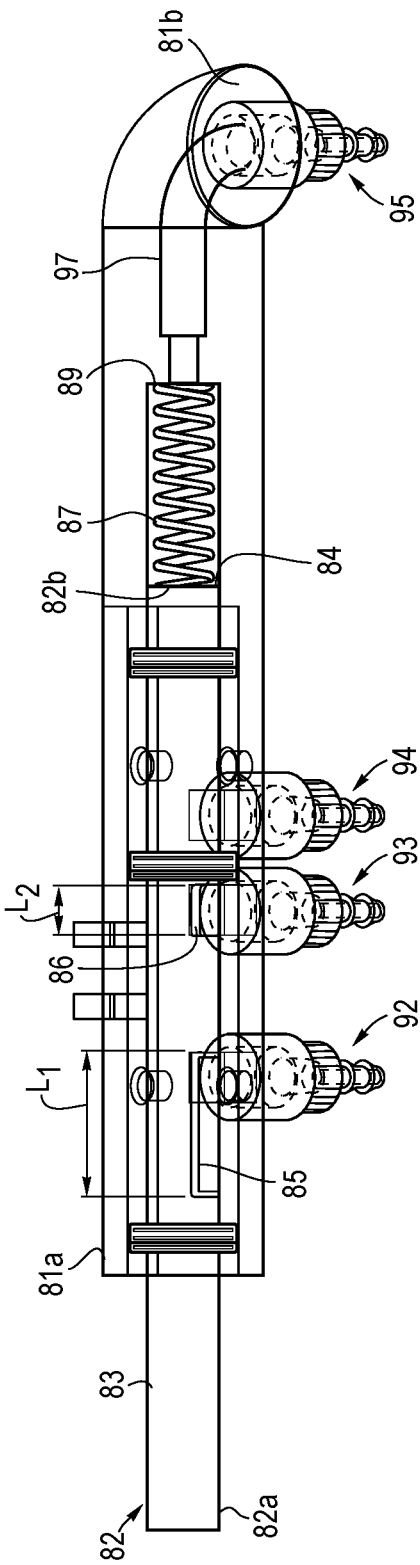

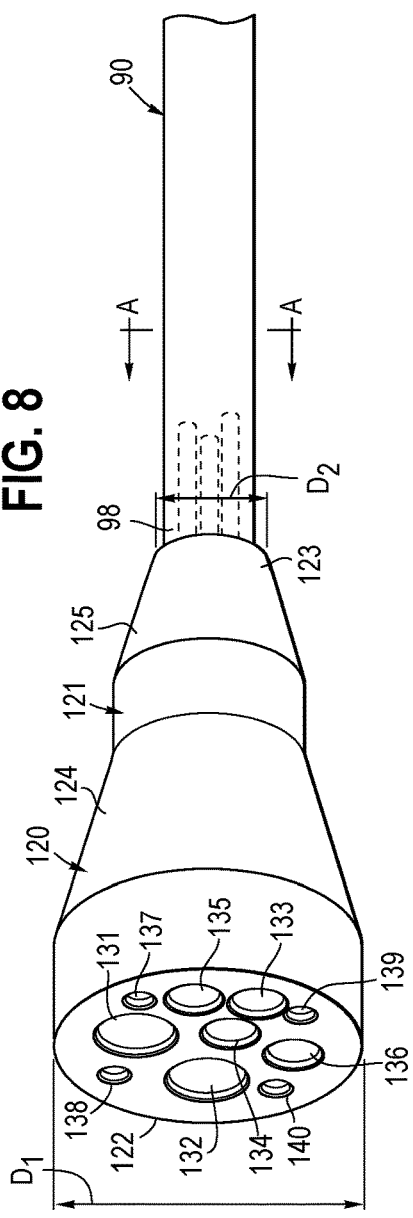
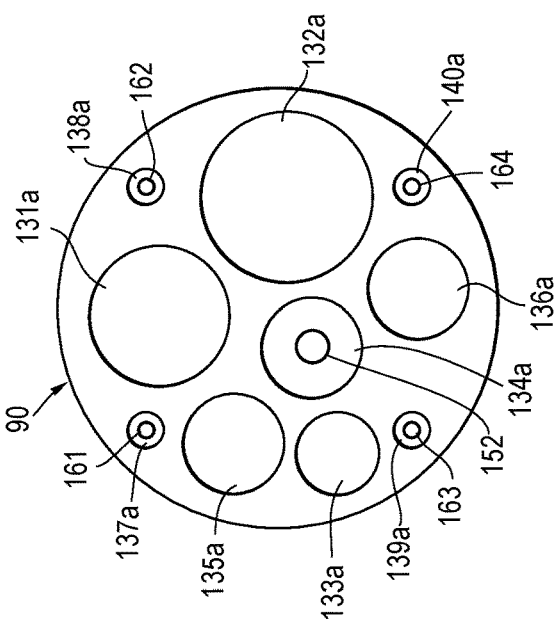
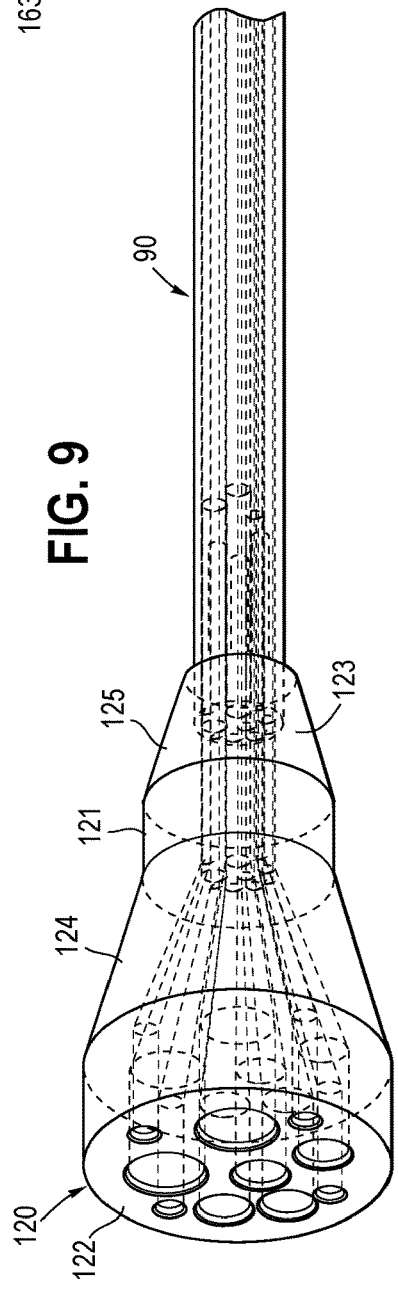
FIG. 8
FIG. 10
FIG. 9

MEDICAL SCOPES FOR DELIVERING THERAPEUTIC AGENTS

PRIORITY CLAIM

This invention claims the benefit of priority of U.S. Provisional Application Ser. No. 63/035,270, entitled "Medical Scopes for Delivering Therapeutic Agents," filed Jun. 5, 2020, the disclosure of which is hereby incorporated by reference in its entirety.

BACKGROUND

The present embodiments relate generally to medical devices, and more particularly, to medical scopes for delivering therapeutic agents to a target site.

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of the therapeutic agents to normal, healthy tissues, which may reduce potentially harmful side effects.

Localized delivery of therapeutic agents has been performed using catheters and similar introducer devices. By way of example, a catheter may be advanced towards a target site within the patient, then the therapeutic agent may be injected through a lumen of the catheter to the target site. Typically, a syringe or similar device may be used to inject the therapeutic agent into the lumen of the catheter. However, such a delivery technique may result in a relatively weak stream of the injected therapeutic agent.

Moreover, it may be difficult or impossible to deliver therapeutic agents in a targeted manner in certain forms, such as a powder form, to a desired site. For example, if a therapeutic powder is held within a syringe or other container, it may not be easily delivered through a catheter to a target site in a localized manner that may also reduce potentially harmful side effects.

Still further, some therapeutic agents are delivered using a catheter advanced through a lumen of a separate medical scope that enables imaging of the target site, such as an endoscope. However, using a separate catheter and medical scope may encompass limitations such as instrument sizes that can fit through the lumen of the scope, transportation of a patient to a specific suite capable of accommodating an endoscopic procedure, and the like.

SUMMARY

The present embodiments provide systems and methods suitable for delivering a therapeutic agent to a target site. In one example, the system comprises a container for holding the therapeutic agent, and a pressure source having pressurized fluid, wherein the pressure source is in selective fluid communication with at least a portion of the container. A catheter is placed in fluid communication with the container, and has a lumen sized for delivery of the therapeutic agent to a target site. A housing is configured to securely retain the container. The system further comprises a camera having a camera head coupled to the catheter, wherein the camera provides a visual image of the target site during delivery of the therapeutic agent In one embodiment, the system comprises a catheter adapter having a main body, a proximal end, and a distal end, wherein the catheter adapter is secured relative to the housing, and the distal end of the catheter adapter is coupled to a proximal end of the catheter. The proximal end of the catheter adapter comprises a first diameter and the distal end of the catheter adapter comprises a second diameter, wherein the first diameter is greater than the second diameter.

In one embodiment, the system comprises a valve assembly having an inlet port and at least first and second outlet ports. Pressurized fluid enters through the inlet port, and in a first state the pressurized fluid is directed through the first outlet port to provide insufflation with the absence of delivery of the therapeutic agent. In a second state, the pressurized fluid is directed through the second outlet port and into the container holding the therapeutic agent to provide delivery of the therapeutic agent.

In one embodiment, a method for delivering a therapeutic agent to a target site comprises actuating a pressure source having pressurized fluid, the pressure source in selective fluid communication with at least a portion of a container that holds a therapeutic agent, wherein a housing is configured to securely retain the container. 7The therapeutic agent is delivered, via the pressurized fluid, through a catheter in fluid communication with the container and a target site. The method further comprises visualizing the target site during delivery of the therapeutic agent using a camera having a camera head coupled to the catheter.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 5-7 are, respectively, a side view, a rotated side view, and a close-up perspective view of a valve assembly for use with the present system, where select outer components are shown in phantom to help illustrate interior features.

FIG. 8 is a perspective view of a catheter adapter coupled to a catheter, where an outer portion of the catheter is shown in phantom to help illustrate interior features.

FIG. 9 is a perspective view of the catheter adapter and the portion of the catheter of FIG. 8, with exterior portions shown in phantom to help illustrate interior features.

FIG. 10 is a cross-sectional view of the catheter, and selected interior components, taken along line A-A of FIG. 8.

DETAILED DESCRIPTION OF THE PREFERRED EMBODIMENTS

Figure 1:
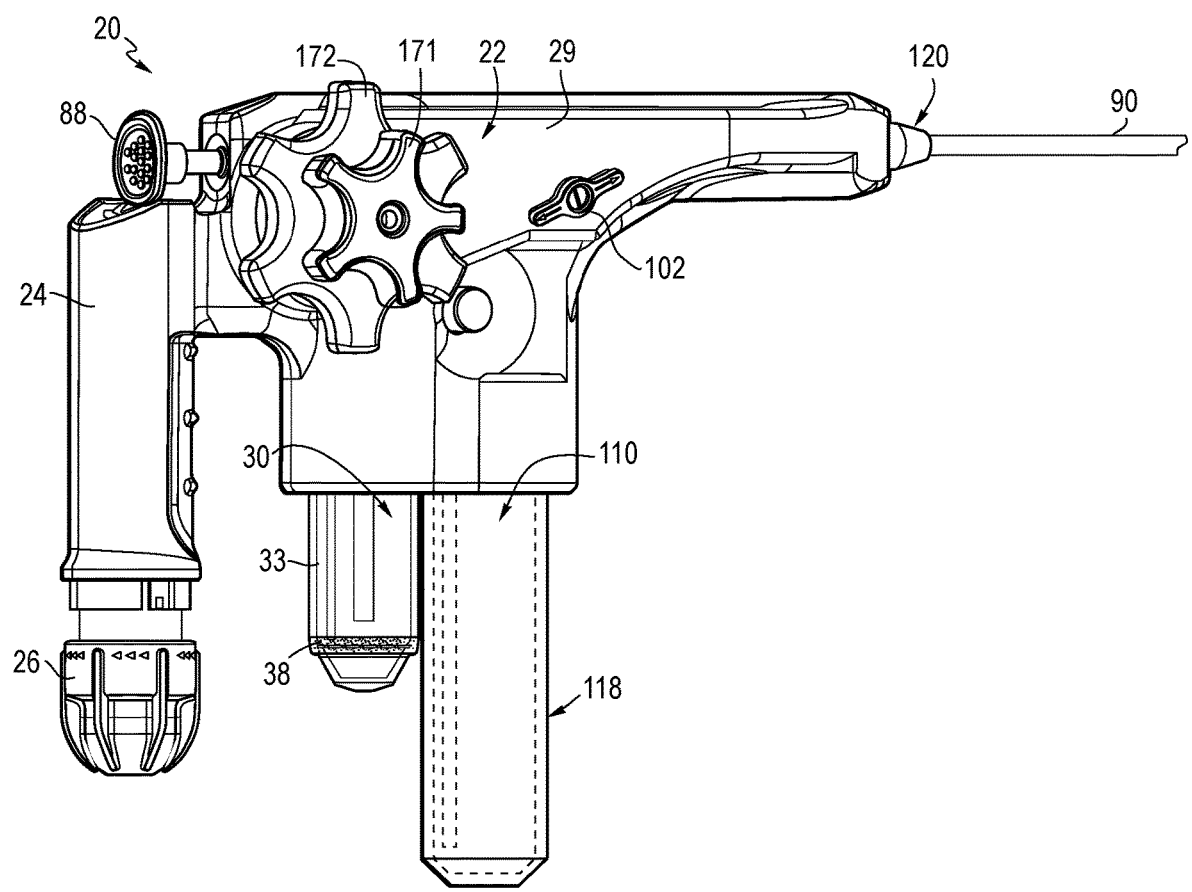
FIG. 1 is a perspective view of a system for delivering therapeutic agents in accordance with a first embodiment.

In the present application, the term "proximal" refers to a direction that is generally towards a physician during a medical procedure, while the term "distal" refers to a direction that is generally towards a target site within a patient's anatomy during a medical procedure.

Referring now to FIGS. 1-4B, a first embodiment of a system 20 suitable for delivering one or more therapeutic agents is shown. In this embodiment, the system 20 comprises a container 30 that is configured to hold a therapeutic agent 38, and further comprises at least one pressure source 68 that is configured to be placed in selective fluid communication with at least a portion of the container 30, to deliver the therapeutic agent 38 through a catheter 90 to a target site within the patient, as explained more fully below.

The system 20 further comprises a housing 22, which is suitable for securely holding, engaging and/or covering the container 30, pressure source 68, catheter 90, and other components described below. Preferably, the housing 22 comprises an upright section 24 that may be grasped by a user and a section 25 for engaging the container 30. An actuator 26 may be engaged by a user and selectively operated to perform the functions described below.

The container 30 may comprise any suitable size and shape for holding the therapeutic agent 38. In FIGS. 1-4B, the container 30 comprises a generally tube-shaped configuration having a first region 31, a second region 32, and a reservoir 33 defined by an interior of the container 30.

Figure 2:
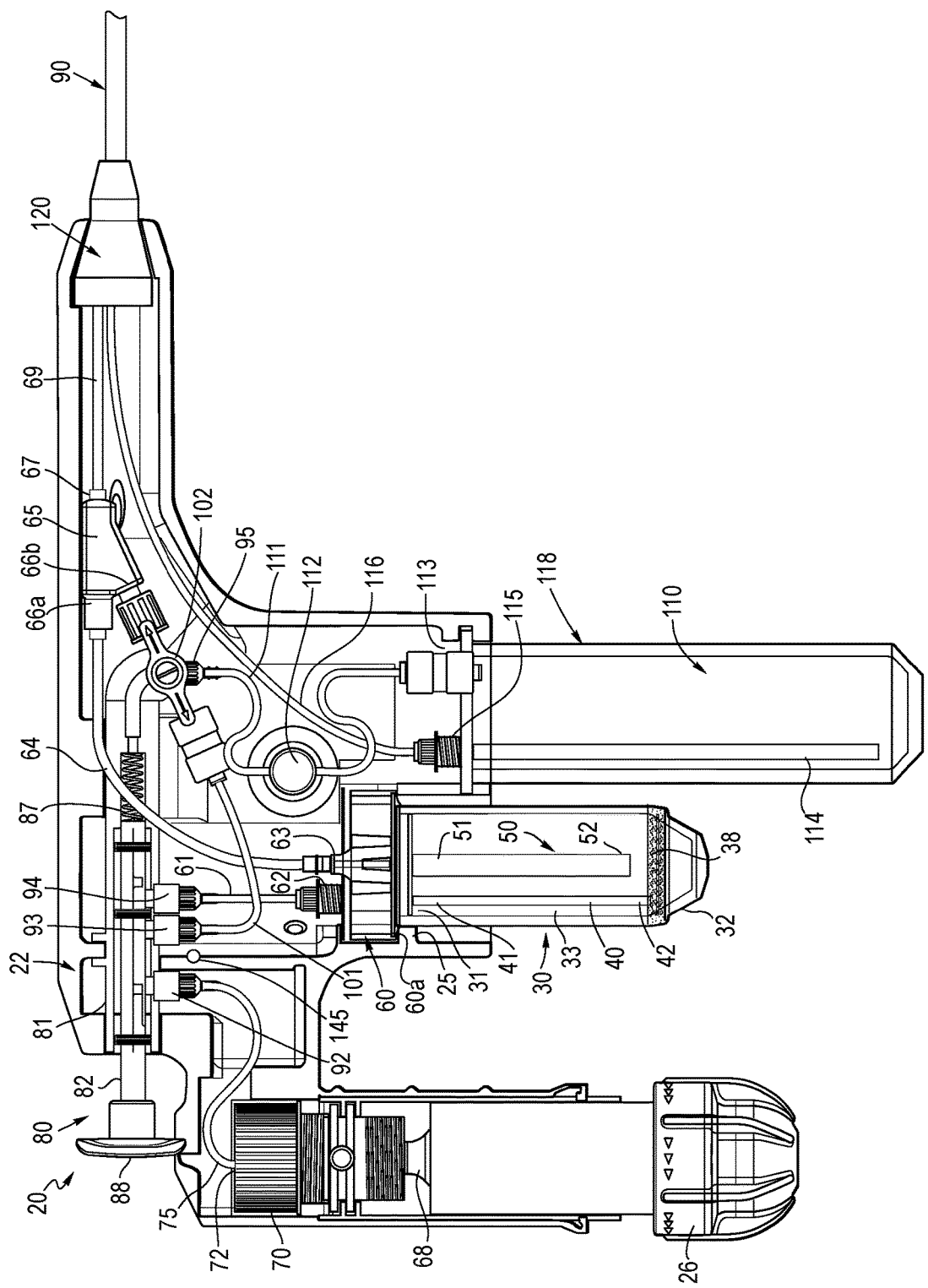
FIG. 2 is a schematic side view of the system of FIG. 1 with a portion of a housing removed.
Figure 3:
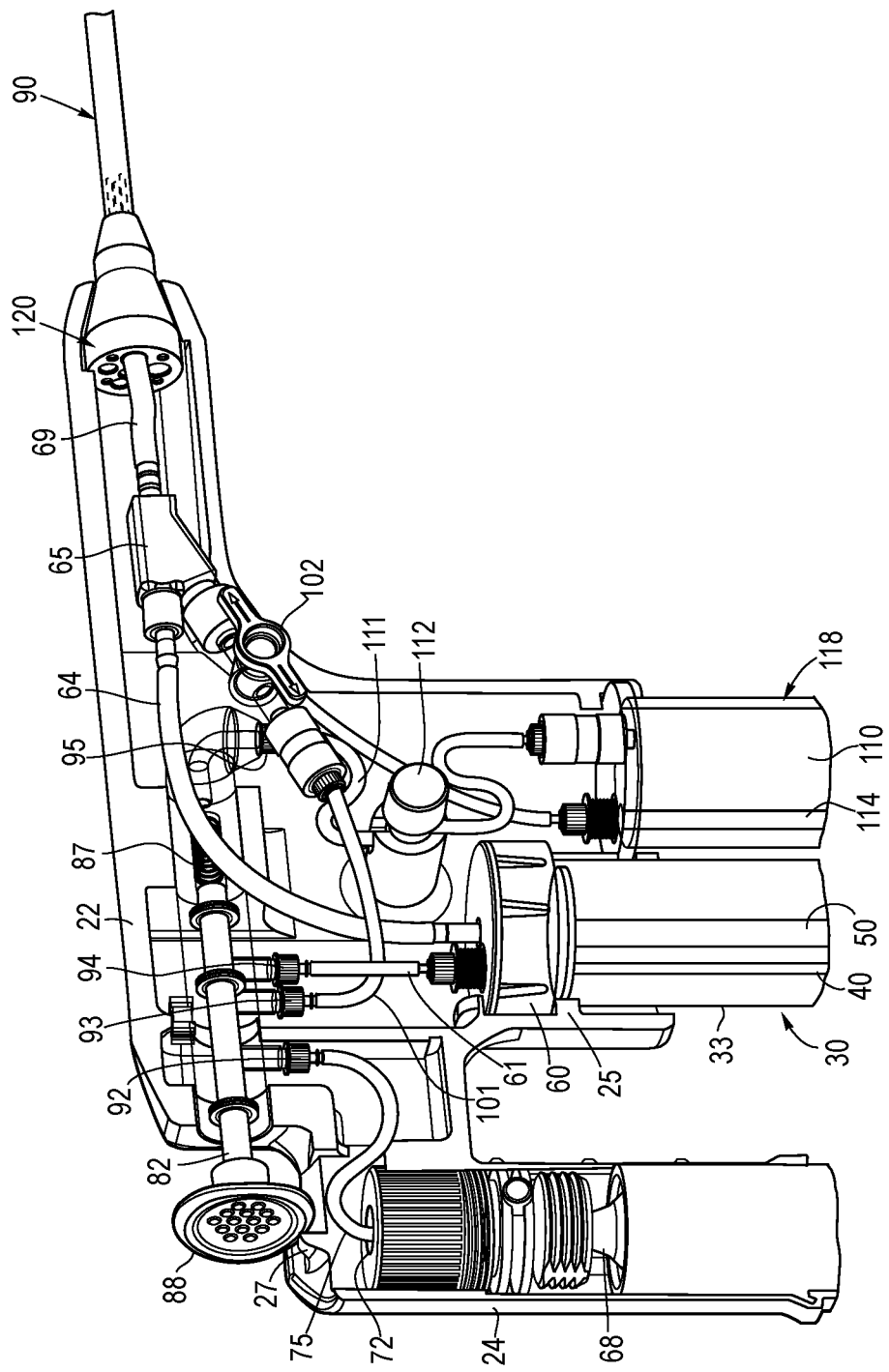
FIG. 3 is a perspective view of the system of FIGS. 1-2 with a portion of a housing removed.

The container 30 may further comprise an inlet tube 40, an outlet tube 50, and a cap 60, wherein the cap 60 is configured to be secured to the first region 31 of the container 30, as best seen in FIGS. 2-3. The inlet tube 40 has first and second ends 41 and 42 with a lumen extending therebetween, while the outlet tube 50 has first and second ends 51 and 52 with a lumen extending therebetween. The first end 41 of the inlet tube 40 is placed in fluid communication with an inlet port 62 formed in the cap 60, while the first end 51 of the outlet tube 50 is placed in fluid communication with an outlet port 63 formed in the cap 60, as shown in FIG. 2.

During operation, fluid passed through the inlet port 62 of the cap 60 is directed through the inlet tube 40 and into the reservoir 33. Notably, the u-shaped curvature near the second region 32 of the container 30 effectively changes the direction of the fluid flow by approximately 180 degrees, such that the fluid originally flows in a direction from the first region 31 of the container 30 towards the second region 32, and then from the second region 32 back towards the first region 31. In the embodiment of FIGS. 1-4B, the first region 31 of the container 30 is disposed vertically above the second region 32 of the container 30 during use, however, it is possible to have different placements of the first and second regions 31 and 32 relative to one another, such that they are disposed at least partially horizontally adjacent to one another.

The second end 52 of the outlet tube 50 may terminate a predetermined distance above the second region 32 of the container 20, as shown in FIGS. 1-2 and 4A-4B. Accordingly, as will be explained further below, when fluid from the pressure source 68 is redirected from the second region 32 towards the first region 31, the fluid and the therapeutic agent 38 within the reservoir 33 may be directed through the outlet tube 50, through the outlet port 63, and towards a target site. Alternatively, the outlet tube 50 may be omitted and the therapeutic agent 38 may flow directly from the reservoir 33 into the outlet port 63. Other variations on the container 30 and the outlet port 63 may be found in U.S. Pat. No. 8,118,777, which is hereby incorporated by reference in its entirety.

Moreover, in some embodiments, a platform may be positioned within the container 30 above a curved portion associated with the second region 32, where the platform forms a substantially fluid tight seal with an inner surface of the container 30, thereby preventing the therapeutic agent 38 that is disposed in the reservoir 33 from reaching the curve at the second region 32, as explained further in U.S. Pat. No. 8,118,777. In such embodiment, the platform may comprise an opening though which fluid from the pressure source 68 is directed via a u-shaped tube disposed at the second region 32, as explained further in the '777 patent.

The cap 60 may comprise any suitable configuration for sealingly engaging the first region 31 of the container 30. In one example, an O-ring is held in place around a circumference of the cap 60 to hold the therapeutic agent 38 within the reservoir 33. The inlet and outlet tubes 40 and 50 may be held in place within the container 30 by one or more support members, such as those explained further in U.S. Pat. No. 8,118,777.

Further, as depicted in FIG. 2, the cap 60 may comprise one or more flanges 60a that permit a secure, removable engagement with a complementary internal region of the section 25 of the housing 22. For example, by rotating the container 30, the flange 60a of the cap 60 may lock in place within the section 25.

Advantageously, in this manner, a first container holding a first therapeutic agent may be coupled to the housing 22 for use with the system 20, and subsequently a second container holding a second composition or agent may be coupled to the housing 22 for use with the system 20. By way of example, and without limitation, in one embodiment the system 20 may be "preloaded" with a first container 30 holding a therapeutic agent in the form of a hemostatic power. At a later time, it may be deemed beneficial to deliver a mucoadhesive composition, in which case the first container 30 may be rotated to disengage its flange 60a from the section 25 of the housing, and then insert a second container 30 into the section 25 of the housing 22 for delivery of the mucoadhesive composition. For the sake of brevity, the formulation in the container 30 will be referred to as a "therapeutic agent 38," although as explained herein certain formulations in a container coupled to the housing 22 may be interchanged or varied and may or may not achieve a therapeutic effect per se.

The pressure source 68 may comprise one or more components capable of producing or furnishing a fluid having a desired pressure. In one embodiment, the pressure source 68 may comprise a pressurized fluid, such as a liquid or gas. For example, as shown in FIGS. 2-3, the pressure source 68 may comprise a pressurized fluid cartridge of a selected gas or liquid, such as carbon dioxide, nitrogen, or any other suitable gas or liquid that may be compatible with the human body. The pressurized fluid cartridge may contain the gas or liquid at a relatively high, first predetermined pressure, for example, around 1,800 psi inside of the cartridge. The pressure source 68 optionally may comprise one or more commercially available components.

The fluid may flow from the pressure source 68 through a pressure regulator, such as regulator valve 70 having a pressure outlet 72, as depicted in FIG. 2, which may reduce the pressure to a lower, second predetermined pressure. The actuator 26 may be actuated to release the fluid from the pressure source 68. For example, a user may rotate the actuator 26, which translates into linear motion via a threaded engagement between the actuator 26 and the housing 22. When the linear advancement is imparted to the pressure source 68, the regulator valve 70 may pierce through a seal of the pressure cartridge to release the high pressure fluid. After the regulator valve 70 reduces the pressure, the fluid may flow from the pressure outlet 72 towards an actuation valve assembly 80 via tubing 75.

Figure 7:
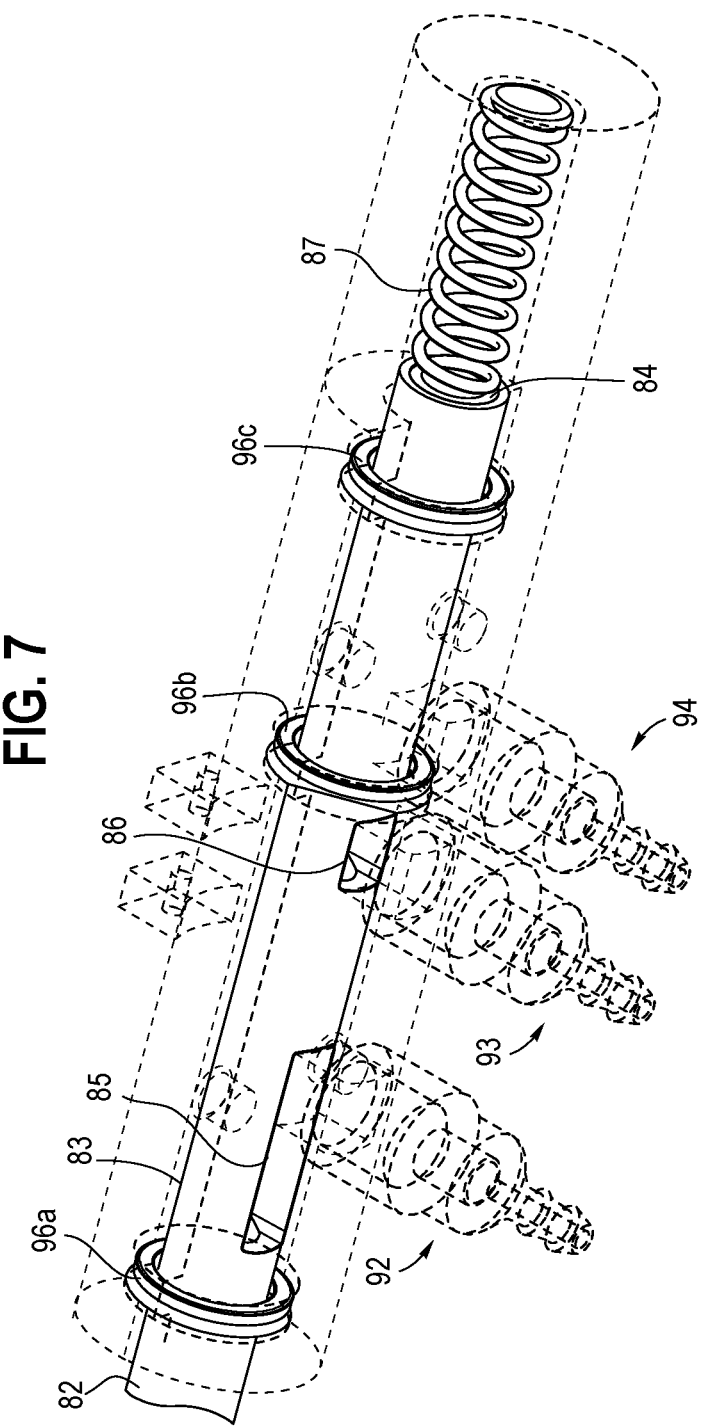
Figure 11:
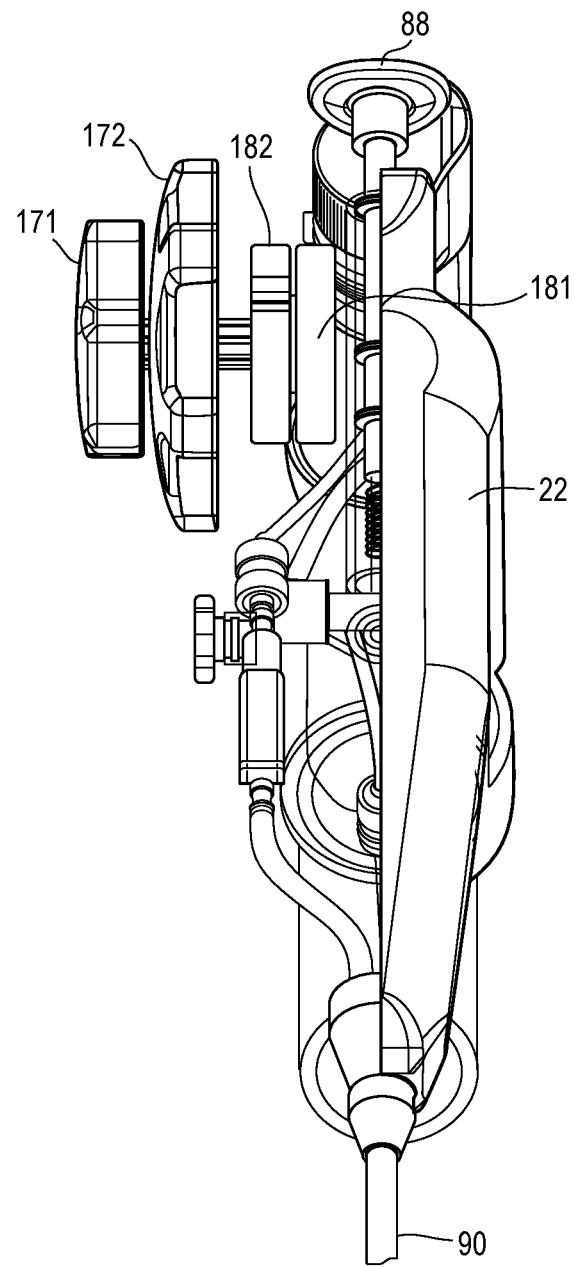
FIG. 11 is a top perspective view of the system of FIG. 1 with a portion of the housing removed to illustrate features of a deflection wire assembly.

Referring to FIGS. 5-7, in conjunction with FIGS. 1-4B, the actuation valve assembly 80 comprises a housing 81 having a proximal region 81a and a distal region 81b, as best seen in FIGS. 5-6. A piston 82, which has proximal and distal regions 82a and 82b, is disposed at least partially within the housing 81. The proximal region 82a of the piston 82 may be coupled to an actuation button 88, as depicted in FIGS. 2-3, thus allowing a user to perform certain functions explained further below. This proximal region 82a of the piston 82 may extend a distance outside of the housing 81, as depicted in FIG. 2, to facilitate coupling to the actuation button 88. The distal region 82b of the piston 82 may be positioned adjacent to a proximal end of a compression spring 87, as depicted in FIGS. 2 and 5-6. In this manner, the piston 82 can be provided with a default position in which the piston 82 is inclined to be disposed further proximally, but if the user applies a sufficient force to the actuation button 88 then the piston 82 can be moved distally against the force of the spring 87, for purposes described below. Notably, the actuation button 88 may abut against a stop member 27 of the housing 22, as best seen in FIG. 3, in order to limit proximal travel of the actuation button 88 such that the piston 82 does not disengage from the actuation valve assembly 80.

Various inlet and outlet ports are associated with the actuation valve assembly 80. In one embodiment, an inlet port 92, and three different outlet ports 93-95, are associated with the actuation valve assembly 80.

The inlet port 92 of the actuation valve assembly 80 may be coupled to the tubing 75 extending from the pressure outlet 72 of the regulator valve 70, as depicted in FIG. 2, thus providing pressurized fluid at a predetermined pressure into the actuation valve assembly 80.

In one embodiment, the piston 82 comprises a generally tubular body 83 having a lumen 84 extending between the proximal and distal regions 82a and 82b, as best seen in FIGS. 6-7. Further, first and second slots 85 and 86 extend through different regions of the tubular body 83 of the piston 82, as seen in FIGS. 5-7.

The first slot 85 of the piston 82 is axially aligned with the inlet port 92 in at least one operational state. The second slot 86 of the piston 82 may be axially aligned with the outlet port 93 in a first state, and further may be axially aligned with the outlet port 94 in a second state, to thereby selectively provide fluid communication between the piston 82 and either the outlet port 93 or the outlet port 94, as explained further below.

When the actuation button 88 is not engaged by a user, the force provided by the compression spring 87 biases the piston 82 to the first state in which the first slot 85 of the piston 82 is axially aligned with the inlet port 92, and further in which the second slot 86 of the piston is axially aligned with the outlet port 93, as depicted in FIGS. 5-7. In this manner, pressurized fluid from the pressure source 68 (as regulated by the regulator valve 70) is directed into the outlet port 93 and into insufflation tubing 101, at which point a user has the option to selectively provide insufflation fluid by actuating a valve 102, for example and without limitation a stopcock or button valve, as explained further below.

When the actuation button 88 is depressed by the user in a manner to overcome the force provided by the compression spring 87, the piston 82 is advanced distally to the second state in which the first slot 85 of the piston 82 remains axially aligned with the inlet port 92, while the second slot 86 of the piston 82 becomes axially aligned with the outlet port 94. In this manner, pressurized fluid from the pressure source 68 (as regulated by the regulator valve 70) is directed into the outlet port 94 and into tubing 61, where it is then directed into the inlet port 62 of the cap 60 and into the container 30 holding the therapeutic agent 38. Notably, one or more sealing members, such as O-rings 96a-96c, may be used to provide a fluid tight seal as the pressurized fluid traverses through the housing 81.

In one embodiment, the first slot 85 comprises a length $L_1$, and the second slot 86 comprises a length $L_2$, where the length $L_1$ is greater than the length $L_2$, as depicted in FIGS.

5-7. Due to its longer length $L_1$, it is possible for the first slot 85 to remain in fluid communication with the inlet port 92 in both the first and second states, i.e., before and after the user depresses the actuation button 88. In contrast, due to its shorter length $L_2$, the second slot 86 moves from being in fluid communication with the outlet port 93 to the outlet port 94 when the user depresses the actuation button 88.

The distal region 82b of the piston 82 may be secured to the proximal end of the compression spring 87, as depicted in FIGS. 5-7. Alternatively, the piston 82 may abut against the compression spring 87 directly without a securement mechanism, or may be coupled in an indirect manner, so long as the spring force is transmitted to the piston 82. In either case, it is preferred that the distal end of the compression spring 87 remains fixed in position relative to the housing 81 of the actuation valve assembly 80. In one embodiment, the compression spring 87 may abut against a non-movable interior flange 89 of the actuation valve assembly 80, as depicted in FIGS. 5-7, which holds the distal end of the compression spring 87 in place.

The lumen 84 of the piston 82 is further in fluid communication with the outlet port 95 of the actuation valve assembly 80, such that pressurized fluid from the pressure source 68 is also delivered through the outlet port 95. In particular, a certain amount of pressurized fluid that enters through inlet port 92 flows distally beyond the first and second slots 85 and 86 in the piston 82, and through the distal region 82b of the piston 82, at which point the pressurized fluid then passes through a space in the interior of the compression spring 87, within the flange 89 that constrains the compression spring 87, and then into a lumen 97 distal to the flange 89, as shown in FIGS. 5-7. Pressurized fluid from the lumen 97 then may exit through the outlet port 95. Pressurized fluid exiting through the outlet port 95 may travel distally into tubing 111 and towards a fluid reservoir 110, as best seen in FIGS. 2-3.

The fluid reservoir 110 may comprise an irrigation fluid disposed in an interior of a container 118. Pressurized fluid traveling from the outlet port 95 and through the tubing 111 may pass through a valve 112 (when in an open state), then through an inlet port 113 associated with the container 118, as best seen in FIG. 2. At this time, the pressurized fluid (which had originated form the pressure source 68) propels the irrigation fluid within the reservoir 110 through an outlet tube 114 and an outlet port 115 associated with the container 118, and then through tubing 116 which ultimately connects to a catheter adapter 120, as explained further below.

Notably, the valve 112 is operable by a user to selectively inhibit flow of the pressurized fluid into the fluid reservoir 110, and consequently this action selectively stops or resumes delivery of the irrigation fluid to the target site. In one embodiment, the irrigation fluid in the fluid reservoir 110 may comprise water or another suitable fluid, which may be used to clean a camera lens associated with the system 20, as explained further below.

Although exemplary ports 92-95 and associated tubing (such as tubing 75, 101, 61 and 111) are depicted in FIG. 1-7, it will be appreciated that other suitable coupling mechanisms may be employed to secure the various pieces of tubing to the various valves and ports.

Referring now to FIGS. 8-10, the system 20 may comprise a catheter adapter 120, for use with the catheter 90, to facilitate direction and routing of component of the system 20 towards the catheter 90. Notably, FIGS. 8-9 provide two views of the catheter adapter 120 (in a proximal to distal facing direction) plus a proximal end 98 of the catheter 90, while FIG. 10 shows a cross-section view of the catheter 90 taken along line A-A of FIG. 8 (facing a distal to proximal direction).

The catheter adapter 120 comprises a main body 121 having a proximal end 122 and a distal end 123, where the proximal end 122 comprises a diameter $D_1$ that is greater than a diameter $D_2$ at the distal end 123. At least one taper may be disposed between the proximal and distal ends 122 and 123 to transition from the larger diameter $D_1$ to the smaller diameter $D_2$. In the embodiment of FIGS. 8-10, two different tapers 124 and 125 are provided between the proximal and distal ends 122 and 123 of the main body 121.

Advantageously, the larger diameter $D_1$ at the proximal end 122 allows for receipt of extensive amounts of tubing and other components, as described herein, while the tapers then facilitate the transition to the smaller diameter $D_2$, which is closer to the diameter of the catheter 90.

In FIGS. 8-9, the catheter adapter 120 comprises lumens 131-140, which are explained further below, and which are in communication with corresponding lumens 131a-140a of the catheter 90. As one example, a therapeutic agent lumen 131 of the catheter adapter 120 of FIGS. 8-9 is in fluid communication with the therapeutic agent lumen 131a of the catheter 90 in FIG. 10. In this manner, there is a direct correspondence between lumens of the catheter adapter 120 and the lumens of the catheter 90.

The tapering of the main body 121 of the catheter adapter 120 accommodates a reduction in the diameter of various lumens by a certain amount, when comparing larger inner diameters of the lumens 131-140 at the proximal end 122 of the catheter adapter 120 with smaller inner diameters of the corresponding lumens of the catheter 90. For example, in one embodiment, the therapeutic agent lumen 131 may comprise a first inner diameter at the proximal end 122 of the catheter adapter 120, and a second, smaller inner diameter in lumen 131a of the catheter 90, where the transition in inner diameters occurs along the catheter adapter 120, as depicted in FIG. 9.

The reduction in inner diameter for the various lumens 131-140 is preferably at least 5% for one or more lumens, and in some embodiments between 10-90% for a given lumen, depending on the lumen and its purpose. It may be clinically important that certain lumens, such as the therapeutic agent lumen 131, do not become reduced too greatly from the first diameter at the proximal end 122 of the catheter adapter 120 relative to its corresponding smaller lumen 131a in the catheter, because too small of a catheter lumen may cause clogging. However, other lumens 131a-140a of the catheter 90 may achieve a considerably smaller diameter if there are no significant drawbacks to a smaller lumen.

As seen in FIGS. 8-10, the catheter adapter 120 comprises the therapeutic agent lumen 131, which is in fluid communication with the container 30 of FIGS. 1-4B that holds the therapeutic agent 38. Referring back to FIG. 2, the outlet port 63 in the cap 60 of the container 30 may be placed in fluid communication with tubing 64, which extends in a distal direction towards a first intake port 66a of a coupler 65, for example and without limitation a y-shaped or t-shaped coupler. An exit port 67 of the coupler 65 is secured to outlet tubing 69, which then extends distally into engagement with the first larger diameter of the therapeutic agent lumen 131 of the catheter adapter 120. Notably, the second intake port 66b of the coupler 65 is in fluid communication with insufflation tubing 101, which extends from the outlet port 93 of the valve assembly 80 as explained above.

Advantageously, in this manner, the therapeutic agent lumen 131 of the catheter adapter 120 and the corresponding lumen 131a of the catheter 90 provide the selective delivery of either the therapeutic agent 38 and pressurized fluid from the pressure source 68, or alternatively only the pressurized fluid from the pressure source 68, depending on whether the second slot 86 of the piston 82 is axially aligned with the outlet port 93 in the first state, or alternatively axially aligned with the outlet port 94 in the second state. This provides for a simple and efficient ability for a user to switch between a therapeutic agent delivery mode or alternatively an insufflation mode (that lacks delivery of the therapeutic agent).

As shown in FIGS. 8-10, the catheter adapter 120 further comprises an aspiration lumen 132, which is in fluid communication with an aspiration source (not shown) via an aspiration aperture 145 provided in the housing 22. In some embodiments, the aspiration source may comprise an external suction pump that is in fluid communication with the aspiration lumen 132 via tubing (not shown) that extends through the aspiration aperture 145. Alternatively, the aspiration source may comprise a turbine or fan that is passively powered and turns on from each actuation of the delivery of the therapeutic agent 38 and pressurized fluid 68, such that air is pulled in through the aspiration lumen 132a of the catheter 90 at the same time as the therapeutic agent 38 and pressurized fluid 68 are expelled from the catheter 90.

Advantageously, the aspiration lumen 132a can provide a suction ability at or near the distal end of the catheter 90 and the target site, which can enable continuous or intermittent suctioning of the pressurized fluid into the catheter 90. This may be beneficial to reduce excessive gas distension from the therapeutic agent delivery mechanism, and may maintain volume and pressure in vivo. Further, the suction ability from the aspiration source, delivered via the aspiration lumen 132a, is advantageous to facilitate clearing out excessive amounts of therapeutic agent 38 that have aerosolized to restore visibility to a user.

If an external pump is used, continuous infusion of propellant and aspiration may be performed. Such continuous infusion may include the benefit of reducing clogging of the pathway for the delivery of the therapeutic agent 38. Further, continuous aspiration may help maintain a steady insufflation volume within the patient, and can be used to aspirate blood from the target site.

Optionally, the system 20 may incorporate a valve (not shown) to close off the provision of aspiration to the aspiration lumen 132a, which will facilitate insufflation of the affected bodily region. Such valve may be useful in a system with a constant positive pressure, i.e., where there is a continuous delivery of the pressurized fluid 68 towards the target site, which may be beneficial to prevent backflow of fluid that could clog the therapeutic agent lumen 131a of the catheter 90. In such a constant positive pressure system, such a valve to selectively permit aspiration will help transition between a general suction mode when in an open position, or an insufflation mode when in a closed position.

Referring still to FIGS. 8-10, the catheter adapter 120 further comprises an irrigation lumen 133, which is in fluid communication with the reservoir 110 of the container 118 of FIGS. 1-4B that holds the irrigation fluid. Referring back to FIG. 2, the outlet port 115 in the cap of the container 118 may be placed in fluid communication with tubing 116, which extends in a distal direction towards the irrigation lumen 131 of the catheter adapter 120, and in turn is placed in fluid communication with the irrigation lumen 131a of the catheter 90. In this manner, the irrigation lumen 131a provides the delivery of the irrigation fluid, driven by the pressurized fluid from the pressure source 68, when the valve 112 is in an open position.

Figure 15:
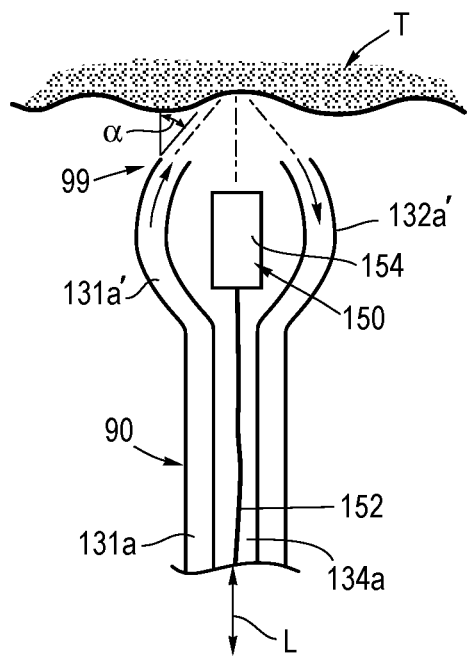
FIG. 15 is a schematic side view depicting a distal region of a therapeutic agent lumen of a catheter being disposed at a non-parallel angle with respect to a distal region of an aspiration lumen of the catheter.
Figure 16:
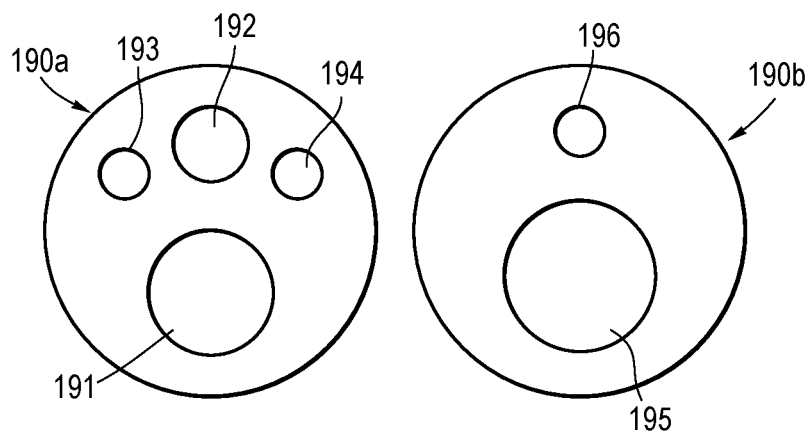
FIG. 16 is a cross-sectional schematic view of an alternative embodiment depicting one exemplary arrangement where a plurality of catheters, each having associated lumens, are used instead of a single catheter.

Referring still to FIGS. 8-10, the catheter adapter 120 further comprises a camera lumen 134 and first and second light transmitting lumens 135 and 136. The camera lumen 134 of the catheter adapter 120, and the corresponding camera lumen 134a of the catheter 90, are dimensioned to receive at least some equipment associated with a camera 150. In one non-limiting embodiment, the camera is wired and comprises a camera cord 152 and a camera head 154, as depicted in the schematic of FIG. 15 (it is noted that several of the lumens of the catheter 90 are omitted in FIG. 15 for illustrative purposes only). In another embodiment, it will be appreciated that the camera can be wireless, and thus the camera cord 152 may be omitted. In the latter example, the camera head 154 may transmit information through a WiFi or other suitable network to image processing or analytic components.

Figure 4A:
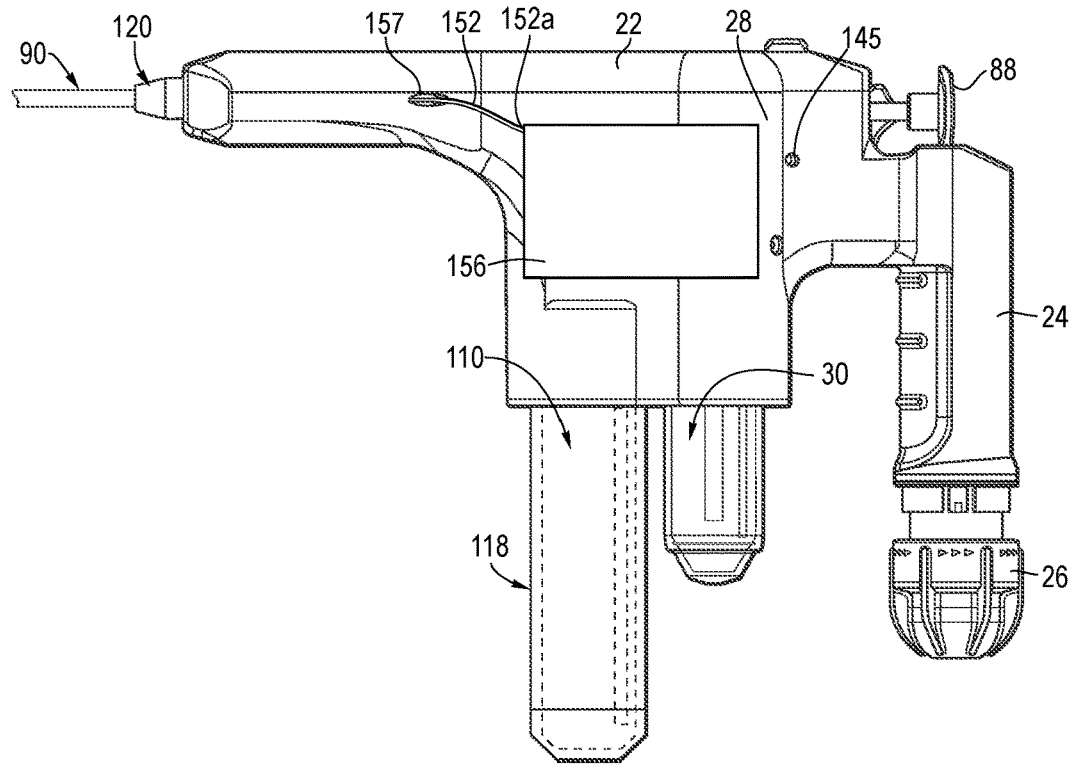
FIG. 4A is a schematic side view of the system of FIGS. 1-3, showing an opposing side of the housing relative to FIG. 1.

The camera 150 has a portion that is held within a camera container 156 that is coupled to the housing 22 of the system. Referring briefly back to FIG. 4A, in one embodiment, the camera container 156 is in the general form of a box that is mounted or otherwise secured to a first side surface 28 of the housing 22. In this example, a proximal region 152a of the camera cord 152 may extend proximally from the camera lumen 134, be routed through an aperture 157 in the first side surface 28 of the housing 22, and into the camera container 156. The proximal region 152a of the camera cord 152 may be coupled to other camera-related equipment stored within the camera container 156, such as image processing equipment or adapters for external coupling. In one example, a suitable cable, such as an HDMI cable, may be connected to a port of the camera container 156, and in turn the HDMI cable can be connected to further image processing or analytic equipment.

In one embodiment, the camera 150 comprises a CMOS camera that facilitates a visual image of the target site T (depicted in FIG. 15) during delivery of the therapeutic agent 38 and other equipment and fluid described herein. The first and second light transmitting lumens 135a and 136a of the catheter 90 provide lighting suitable for high-resolution imaging using the camera head 154. The light transmitting lumens may enable the provision of a light transmitting component, which in one example and without limitation may comprise one or more LEDs. In one example, two LEDs may be provided (one per lumen 135a and 136a) with wires operably coupled, where the wires extend proximally back towards a power source. In various non-limiting embodiments, the power source may comprise a battery, or alternatively power may be drawn from equipment in or coupled to the camera container 156. In one non-limiting example, power may be provided through an HDMI cable coupled to the camera container 156, in which case the wires may be operably coupled to a circuit in the camera container 156 and may receive power from the HDMI cable. Preferably, the first and second light transmitting lumens 135a and 136a are generally positioned on opposing sides of the camera lumen 134a, as depicted in FIG. 10, since providing illumination on only one side of the camera 150 may provide insufficient lighting or contrast on an image.

Referring to FIGS. 11-14, in conjunction with FIGS. 8-10, the system 20 further comprises at least one deflection wire having proximal and distal regions, wherein the proximal region is coupled to a deflection actuator at the housing, and wherein the distal region extends through a deflection wire lumen of the catheter to provide the ability to maneuver a distal region of the catheter upon actuation of the deflection actuator.

In one embodiment, four different deflection wires 161-164 are disposed through respective deflection wire lumens 137a-140a of the catheter 90, as depicted in FIG. 10. The deflection wires 161-164 extend, in a distal to proximal direction, from spaced-apart engagement points at the distal end 99 of the catheter 90, through the respective deflection wire lumens 137a-140a of the catheter 90, through respective deflection wire lumens 137-140 of the catheter adapter 120, and then extend through an interior space of the housing 22 until the proximal regions of the deflection wires 161-164 approach deflection actuators 171 and 172, which can be engaged by a user to selectively maneuver the deflection wires.

Figure 4B:
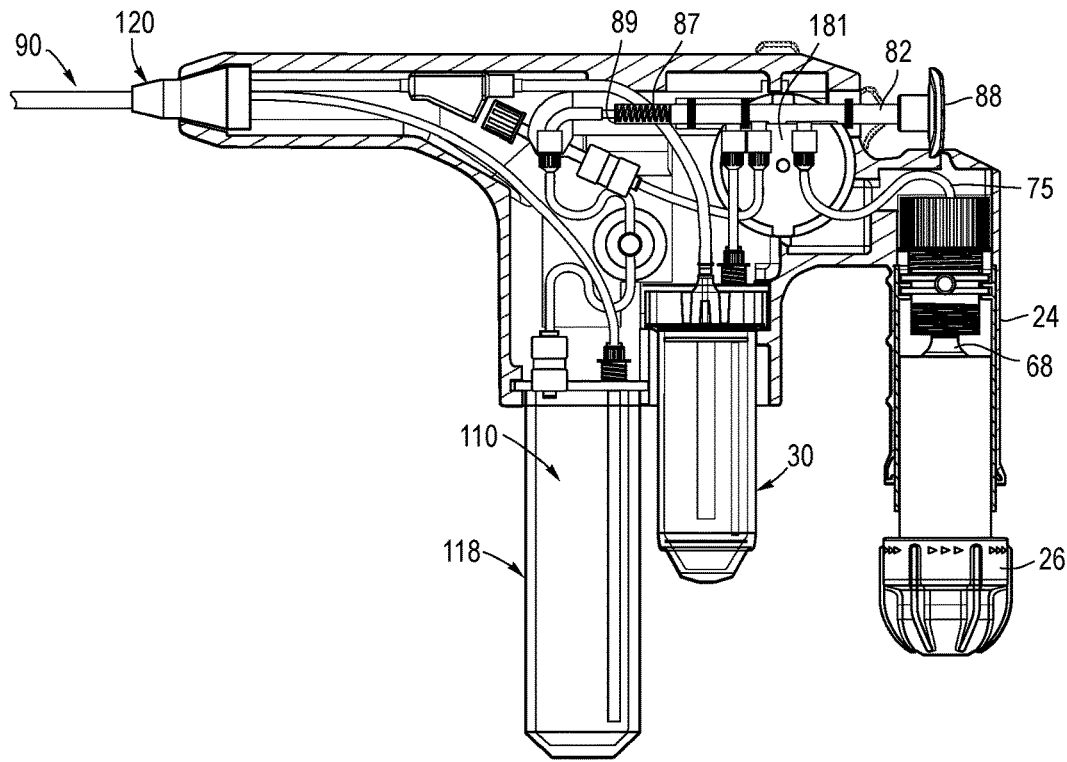
FIG. 4B is a schematic side view of the system of FIG. 1 with a portion of the housing removed, taken from an opposing direction relative to FIG. 2.

In FIGS. 11-14, first and second wire followers 181 and 182 are coupled between the deflection actuators 171 and 172 and the deflection wires 161-164. The first and second wire followers 181 and 182 may be disposed internal to the housing 22, as best seen in FIG. 4B and depicted in FIG. 11, while the deflection actuators 171 and 172 may be disposed external to the housing 22. In one embodiment shown herein, the deflection actuators 171 and 172 are disposed on a second side surface 29 of the housing 22, i.e., a side surface that opposes the first side surface 28 to which the camera container 156 is secured, although it will be appreciated that the deflection actuators 171 and 172 may be disposed on the same surface 28 as the camera container 156, or at another location on or near the housing 22.

Figure 12:
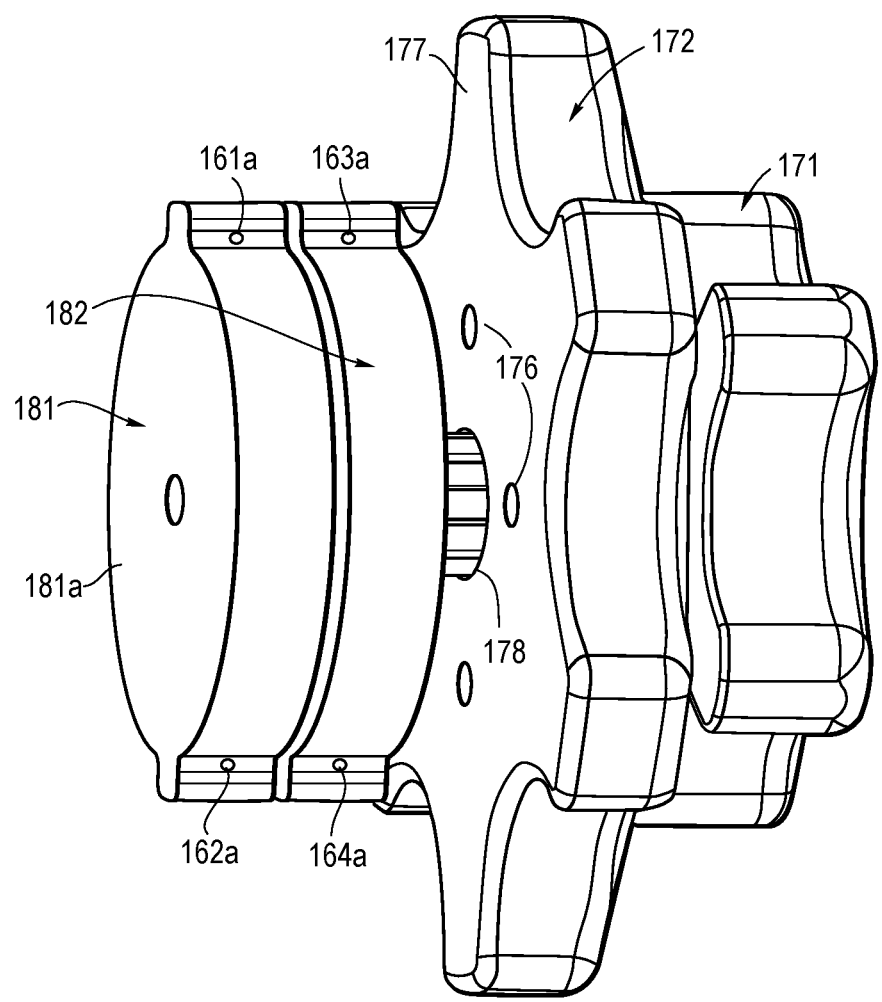
FIG. 12 is a perspective view illustrating deflection actuators and wire followers according to one embodiment.
Figure 13:
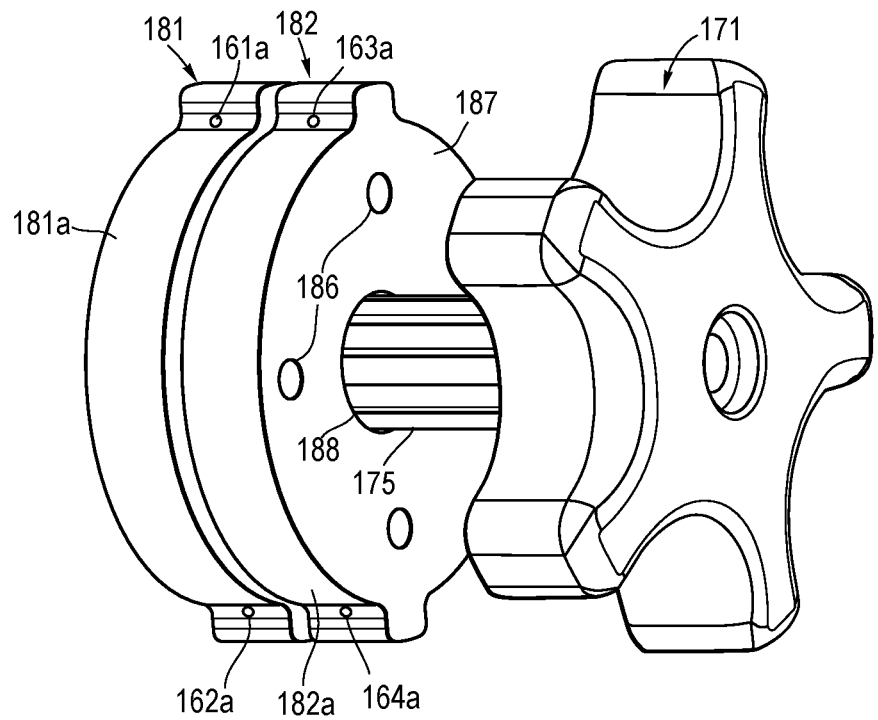
FIG. 13 is a perspective view illustrating the deflection actuators and wire followers of FIG. 12, taken from an opposing angle relative to FIG. 12 and with one of the deflection actuators omitted for illustrative purposes.

As shown in FIGS. 12-13, the first wire follower 181 may comprise a main body 181a, and further may comprise a first coupling region 161a to which a proximal end of the first deflection wire 161 can be secured. The first wire follower 181 further comprises a second coupling region 162a to which a proximal end of the second deflection wire 162 can be secured. In this example, the first coupling region 161a is disposed about 180 degrees apart on the main body 181a relative to the second coupling region 162a, as depicted in FIGS. 12-13.

Figure 14:
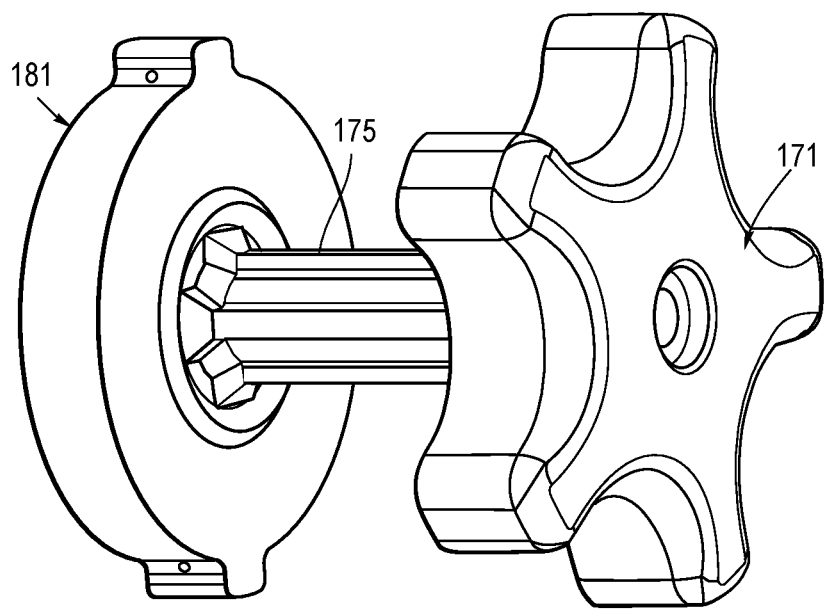
FIG. 14 is a perspective view illustrating coupling of one of the deflection actuators and one of the wire followers of FIGS. 11-12.

The first deflection actuator 171 is operably coupled to the first wire follower 181 such that when the first deflection actuator 171 is rotated in a particular circumferential direction, it achieves a corresponding circumferential rotation of the first wire follower 181. In one example, a torque shaft 175 extends laterally between the first deflection actuator 171 and the first wire follower 181, as shown in FIG. 14. The torque shaft 175 may be formed integrally with the first deflection actuator 171 and the first wire follower 181, or may comprise one or more linkages or other mechanical components that transmit the circumferential motion applied to the first deflection actuator 171 upon the first wire follower 181.

Similarly, the second wire follower 182 may comprise a main body 182a, and further may comprise a third coupling region 163a to which a proximal end of the third deflection wire 163 can be secured. The second wire follower 182 further comprises a fourth coupling region 164a to which a proximal end of the fourth deflection wire 164 can be secured. In this example, the third coupling region 163a is disposed about 180 degrees apart on the main body 182a relative to the fourth coupling region 162b, as depicted in FIGS. 12-13.

The second deflection actuator 172 is operably coupled to the second wire follower 182 such that when the second deflection actuator 172 is rotated in a particular circumferential direction, it achieves a corresponding circumferential rotation of the second wire follower 182. In one example, the second deflection actuator 172 may be provided with a plurality of pin holes 176 formed in an inward surface 177, and the second wire follower 182 may be provided with a plurality of pin holes 186 on a surface 187 facing inward, as depicted in FIGS. 12-13. A plurality of pins, such as dowel pins (not shown), may extend between the plurality of pin holes 176 and 186 in the respective parts. Therefore, in this manner, a circumferential motion applied to the second deflection actuator 172 is imparted upon the second wire follower 182. It should be noted that, in this embodiment, the second deflection actuator 172 and the second wire follower 182 comprise central apertures 178 and 188, respectively, which are each disposed around an outer surface of the torque shaft 175 connecting the first deflection actuator 171 and the first wire follower 181, as depicted in FIGS. 12-13.

In one example, rotation of the first deflection actuator 171 in a first direction causes a corresponding circumferential movement of the first wire follower 181, which may impart a tensile force upon the first deflection wire 161 to move the distal end 99 of the catheter 90 in an upward direction. Conversely, rotation of the first deflection actuator 171 in an opposing second direction causes circumferential movement of the first wire follower 181 in the second direction, which may impart a tensile force upon the second deflection wire 162 to move the distal end 99 of the catheter 90 in a downward direction.

Further, rotation of the second deflection actuator 172 in a first direction causes a corresponding circumferential movement of the second wire follower 182, which may impart a tensile force upon the third deflection wire 163 to move the distal end 99 of the catheter 90 in a left-to-right direction. Conversely, rotation of the second deflection actuator 172 in an opposing second direction causes circumferential movement of the second wire follower 182 in the second direction, which may impart a tensile force upon the fourth deflection wire 164 to move the distal end 99 of the catheter 90 in a right-to-left direction.

In this manner, the four deflection wires 161-164 can move the distal end 99 of the catheter 90 in four distinct directions, which will facilitate imaging at the target site T by the camera head 154.

Referring to FIG. 15, in this embodiment a distal region 131a' of the therapeutic agent lumen 131a of the catheter 90 may be disposed at a non-parallel angle with respect to a distal region 132a' of the aspiration lumen 132a of the catheter 90. Advantageously, such technique may reduce the likelihood of having the therapeutic agent 38 repel off the target site T back towards the camera 150 in a manner that can obscure the camera view, or otherwise engage the camera in a manner that can disable its functions.

In the example of FIG. 15, the distal region 131a' of the therapeutic agent lumen 131a is disposed at an angle α relative to a main longitudinal axis L of the catheter 90. The angle α may be in the range of about 5 degrees to about 75 degrees, and more preferably is in the range of about 20 to about 60 degrees. The distal region 132a' of the aspiration lumen 132a may be disposed the same angle α relative to the main longitudinal axis L, or alternatively may be disposed at a different angle, but in either case the non-parallel alignment of distal regions 131a' and 132a' of these particular lumens may improve visualization by the camera.

In operation, the distal end 99 of the catheter 90 may be positioned in relatively close proximity to the target site. The catheter 90 may be advanced to the target site using an open technique, an intraluminal technique, through the mouth, colon, nostrils or using any other suitable technique, and the camera 150 may facilitate positioning at the target site.

When the catheter 90 is positioned at the desired target site, the pressure source 68 may be actuated by engaging the actuator 26. As noted above, the pressurized fluid may flow from the pressure source 68 through a regulator valve 70 and be brought to a desired pressure and rate. It will be appreciated that any passive flow regulator may be used to bring the pressurized fluid to the desired parameters. The fluid then flows through the tubing 75 and into the actuation valve assembly 80 via the inlet port 91.

The pressurized fluid then flows through the outlet ports 93 and 95 when the actuation button 88 is in its relaxed state. At this time, the user has the option to selectively provide insufflation fluid by actuating the valve 102 given the pressurized fluid is available through the outlet port 93.

When the user desires to deliver the therapeutic agent 38, the user depresses the actuation button, thereby overcoming the force from the compression spring 87 and aligning the second slot 86 of the plunger 82 with the outlet port 94. At this time, the regulated pressurized fluid flows through the outlet port 94 and through the tubing 61 towards the container 30. The fluid is then directed through the inlet port 62, through the inlet tube 40 within the container 30, and then the direction of pressurized fluid is redirected upward at the bottom of the container 30. Regulated fluid then urges the therapeutic agent 38 through the outlet tube 50. The fluid and the therapeutic agent 38 then exit through the first end 51 of the outlet tube 50, through the outlet port 63 of the cap 60, then thorough the coupler 65, the catheter adapter 120 and the ultimately through the catheter 90, as explained in detail above, thereby delivering the therapeutic agent 38 to the target site at a desired pressure.

The system 20 may be used to deliver the therapeutic agent 38 in a wide range of procedures and the therapeutic agent 38 may be chosen to perform a desired function upon ejection from the distal end of the catheter 90. Solely by way of example, and without limitation, the provision of the therapeutic agent 38 may be used for providing hemostasis, closing perforations, performing lithotripsy, treating tumors and cancers, treat renal dialysis fistulae stenosis, vascular graft stenosis, and the like. The therapeutic agent 38 can be delivered during procedures such as coronary artery angioplasty, renal artery angioplasty and carotid artery surgery, or may be used generally for treating various other cardiovascular, respiratory, gastroenterology or other conditions. The above-mentioned systems also may be used in transvaginal, umbilical, nasal, and bronchial/lung related applications.

For example, if used for purposes of hemostasis, thrombin, epinephrine, or a sclerosant may be provided to reduce localized bleeding. Similarly, if used for closing a perforation, a fibrin sealant may be delivered to a localized lesion. In addition to the hemostatic properties of the therapeutic agent 38, it should be noted that the relatively high pressure of the fluid and therapeutic agent, by itself, may act as a mechanical tamponade by providing a compressive force, thereby reducing the time needed to achieve hemostasis.

The therapeutic agent 38 may be selected to perform one or more desired biological functions, for example, promoting the ingrowth of tissue from the interior wall of a body vessel, or alternatively, to mitigate or prevent undesired conditions in the vessel wall, such as restenosis. Many other types of therapeutic agents 38 may be used in conjunction with the system 20.

The therapeutic agent 38 may be delivered in any suitable form. For example, the therapeutic agent 38 may comprise a powder, liquid, gel, aerosol, or other substance. Advantageously, the pressure source 68 may facilitate delivery of the therapeutic agent 38 in any one of these forms.

The therapeutic agent 38 employed also may comprise an antithrombogenic bioactive agent, e.g., any bioactive agent that inhibits or prevents thrombus formation within a body vessel. Types of antithrombotic bioactive agents include anticoagulants, antiplatelets, and fibrinolytics. Anticoagulants are bioactive materials that act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Additionally, or alternatively, the therapeutic agent 38 may include thrombolytic agents used to dissolve blood clots that may adversely affect blood flow in body vessels. A thrombolytic agent is any therapeutic agent that either digests fibrin fibers directly or activates the natural mechanisms for doing so. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA. The therapeutic agent 38 may comprise coating-forming agents to protect or assist in healing of lesions and/or wounds.

However, while a few exemplary therapeutic agents 38 have been described, it will be apparent that numerous other suitable therapeutic agents may be used in conjunction with the system 20 and delivered through the catheter 90.

Advantageously, the system 20 permits localized delivery of a desired quantity of the therapeutic agent 38 at a desired, regulated pressure. Since the distal end of the catheter 90 may be placed in relatively close proximity to a target site, the system 20 provides significant advantages over therapeutic agents delivered orally or through an IV system and may reduce accumulation of the therapeutic agent 38 in healthy tissues, thereby reducing side effects. Moreover, the delivery of the therapeutic agent 38 to the target site is performed in a relatively fast manner due to the relatively high pressure of the fluid, thereby providing a prompt delivery to the target site compared to previous devices.

Figure 17:
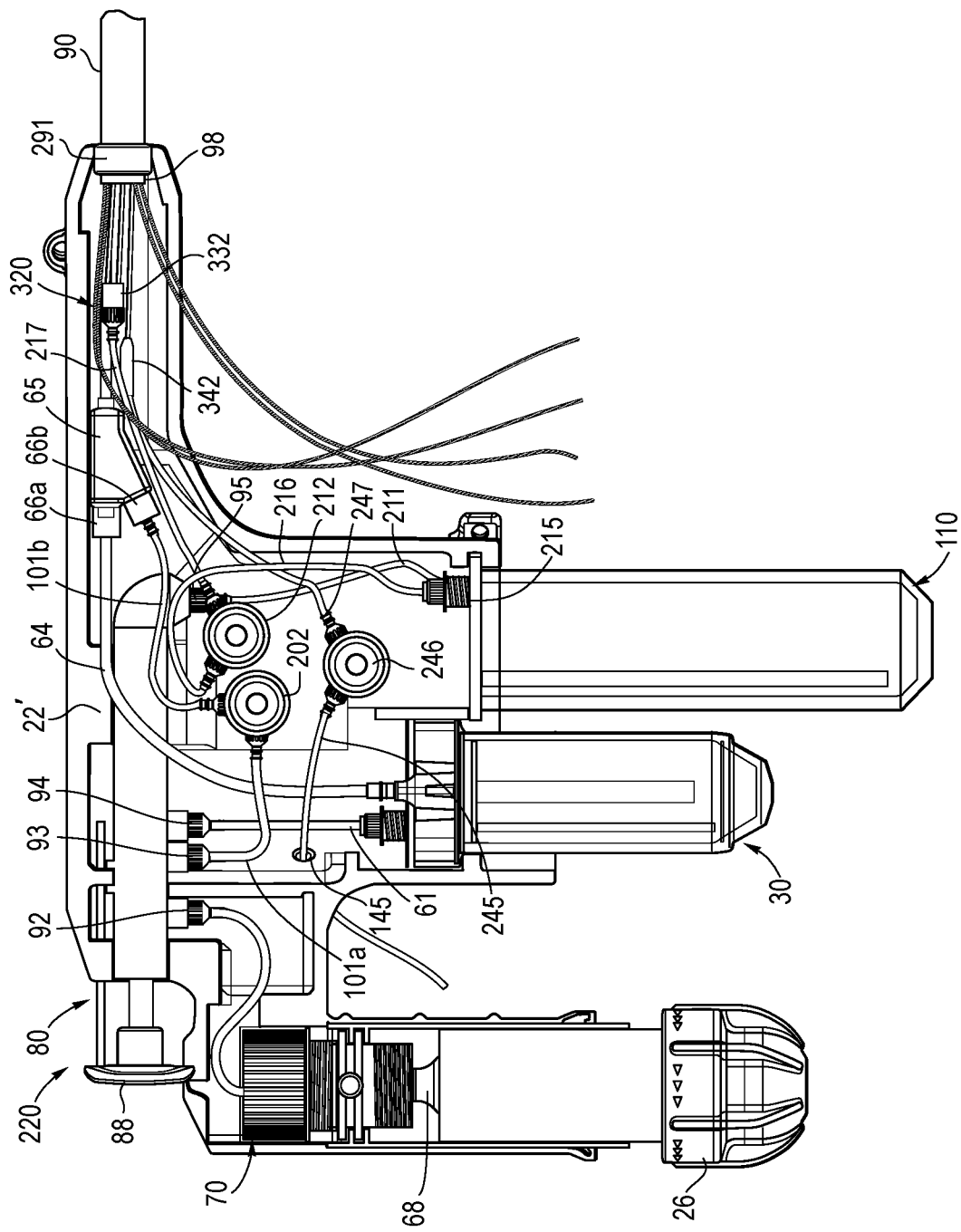
FIG. 17 is a side view of a system for delivering therapeutic agents in accordance with an alternative embodiment, with a portion of a housing and deflection actuators removed for illustrative purposes.

The therapeutic agent 38 may have a specific range of properties that make it suitable for delivery through the catheter 90. In particular, the mass of an individual particle of the therapeutic agent 38 should be within a specific range. If a particle of the therapeutic agent 38 is too heavy, it will require too much pressure to travel the length of the catheter 90 and can result in clogging of the catheter 90. If the particle is too light, it will aerosolize within the patient's body, e.g., in the gastrointestinal space, instead of being propelled to a target site. In addition to mass of an individual particle of the therapeutic agent 38, the size of the particle is important for ensuring proper delivery through the catheter 90. If the particle of the therapeutic agent 38 is too large in size, then it will be prone to clogging within the delivery catheter 90. If the particle is too small, it may have a higher likelihood of being aerosolized instead of being propelled to the target site. Details of suitable properties for the therapeutic agent 30 relative to the catheter 90, which are expected to reduce the likelihood of events such as aerosolization of the particles and clogging of the catheter, are described in U.S. Pat. No. 9,867,931, which is hereby incorporated by reference in its entirety.

Additional steps of operation of the system 20 have been described above. For example, the user may optionally apply suction via the aspiration lumen 132*a*, may selectively provide irrigation fluid via the irrigation lumen 133*a* (when the irrigation valve 112 is in an open position) to help clean the camera 150, and may engage the deflection actuators 171 and 172 to selectively maneuver the deflection wires 161-164, thereby moving the distal end of the catheter 90 in at least four distinct directions, as explained in detail above.

Advantageously, in the system 20, because a camera 150 is provided as part of the system, including a dedicated lumen in the catheter 90, a separate visualization system such as an endoscope is not required. In this manner, the system 20 can be used as a stand-alone therapeutic agent delivery system with its own imaging capabilities, and is not required to be delivered through a lumen of a separate scope, such as an endoscope.

As a related advantage, the system 20 therefore is not impacted by instrument sizes that can fit through the lumen of a conventional scope. Moreover, since the catheter 90 is not required to be delivered through a conventional scope, transportation of a patient to a specific suite capable of accommodating an endoscopic procedure may be avoided.

Referring now to FIG. 16, in an alternative embodiment, the catheter 90 may be substituted for a plurality of catheters 190*a* and 190*b*. It should be noted that, in FIG. 16, the general components and operation is the same as for the system 20, with selected differences noted below.

In the embodiment of FIG. 16, instead of the catheter 90 carrying all of the lumens 131-140 associated with the system 20, as explained above, the catheters 190*a* and 190*b* may each comprise a fewer number of selected lumens. As one example, and without limitation, the catheter 190*a* may comprise a therapeutic agent lumen 191, a camera lumen 192, a light transmitting lumen 193, and at least one deflection wire lumen 194. The catheter 190*b* may comprise an aspiration lumen 195, and at least one deflection wire lumen 196.

The system FIG. 16 may be particularly advantageous in a transnasal delivery approach. In this example, each catheter 190*a* and 190*b* may be passed through one nostril, such that it effectively becomes a two-nostril delivery system. The catheters 190*a* and 190*b* may be joined together by a manifold or holder outside of the nose so they are stabilized. The particular lumens in each of the catheters 190*a* and 190*b* can be re-arranged without departing from the spirit of the present embodiments, e.g., each catheter 190*a* and 190*b* may comprise greater or fewer lumens, spanning the different types of lumens noted above. For example, it may be beneficial to provide the aspiration lumen 195 in a catheter with fewer lumens (as shown in FIG. 16) to maximize suction ability, but in alternative embodiments the camera lumen (or other lumens) may be in the same catheter as the aspiration lumen.

Advantageously, the system of FIG. 16 provides a delivery system that is ready-to-use in an emergency setting where the patient does not have to be intubated since it is not an endoscopy procedure. Such system may be stocked in an emergency room of a hospital, or non-hospital setting, and may expedite treatment and prevent potential complications associated with intubation and conscious sedation. It should also be noted that any of the embodiments above may be delivered transorally and may avoid the need for intubation in scenarios where the catheter is a small enough diameter, for example and without limitation, about 6 mm or less.

Referring to FIGS. 17-21, an alternative embodiment of a system 220 for delivering therapeutic agents is shown and described. The alternative system 220 is similar to the system 20 described in detail above, with notable exceptions referenced below. It should be noted that FIGS. 17-18 are side and perspective views of the alternative system 220 with a portion of a housing 22' and the deflection actuators 171 and 172 removed for illustrative purposes, although these components appear in FIGS. 19-20.

In the embodiment of FIGS. 17-21, a first valve 202 is provided for selectively permitting flow of insufflation fluid, a second valve 212 is provided for selectively permitting flow of irrigation fluid, and a third valve 246 is provided for selectively permitting flow of an aspiration fluid. The first and second valves 202 and 212 generally correspond to the earlier described valves 102 and 112, which regulate insufflation fluid and irrigation fluid, respectively. In FIGS. 17-21, the valves 202, 212 and 246 may comprise, for example and without limitation, a stopcock or button valve, as generally explained above, or other valve types suitable for regulating the fluid flowing therethrough.

As seen in FIG. 17, pressurized fluid from the pressure source 68 (as regulated by the regulator valve 70) is directed through inlet port 92 and selectively directed into the outlet port 93 (as explained in detail above), then into insufflation tubing 101*a*, at which point a user has the option to selectively provide insufflation fluid by actuating the valve 202. Similar to the embodiments described above using the valve 102, upon actuation of the valve 202, insufflation fluid flows through outlet tubing 101*b* and toward the catheter 90, as explained further below.

In FIGS. 17-21, pressurized fluid from the pressure source 68 is further in fluid communication with the outlet port 95 of the actuation valve assembly 80, via the lumen 84 of the piston 82, in the manner described in FIGS. 2-3 and 5-7 above. However, in the embodiment of FIGS. 17-18, fluid exiting from the outlet port 95 is directed into alternative irrigation tubing 211 that is placed directly in communication with inlet port 213 associated with reservoir 110 holding irrigation fluid, without an intervening valve. Fluid exiting from reservoir 110 then is directed through outlet port 215 and into the valve 212 via tubing 216, and as described above, the valve 212 allows for selective flow of the irrigation fluid therethrough. When irrigation fluid is allowed to pass beyond valve 212, the irrigation fluid then flows into outlet tubing 217 and towards catheter 90, as will be explained further below.

Notably, in the embodiment of FIGS. 17-21, the irrigation valve 212 is disposed downstream relative to the reservoir 110, as contrasted with the embodiment of FIGS. 1-3 where the irrigation valve 112 was disposed upstream relative to the reservoir 110. It will be appreciated that a user may switch the position of a valve, such as the valves 202, 212 and 246, to be either upstream or downstream of certain reservoirs, tubing or other components, without departing from the spirit of the present embodiments.

In FIGS. 17-21, aspiration fluid provided by an aspiration source (not shown) may be directed through tubing 245, which passes through the aspiration aperture 145 provided in the housing 22', as seen in FIG. 17. The tubing 245 is coupled to an inlet port of the valve 246, as depicted in FIG. 17, such that the valve 246 allows for selective flow of the aspiration fluid therethrough. When aspiration fluid is allowed to pass beyond valve 246, the aspiration fluid then flows into outlet tubing 247 and towards catheter 90, as will be explained further below.

Figure 18:
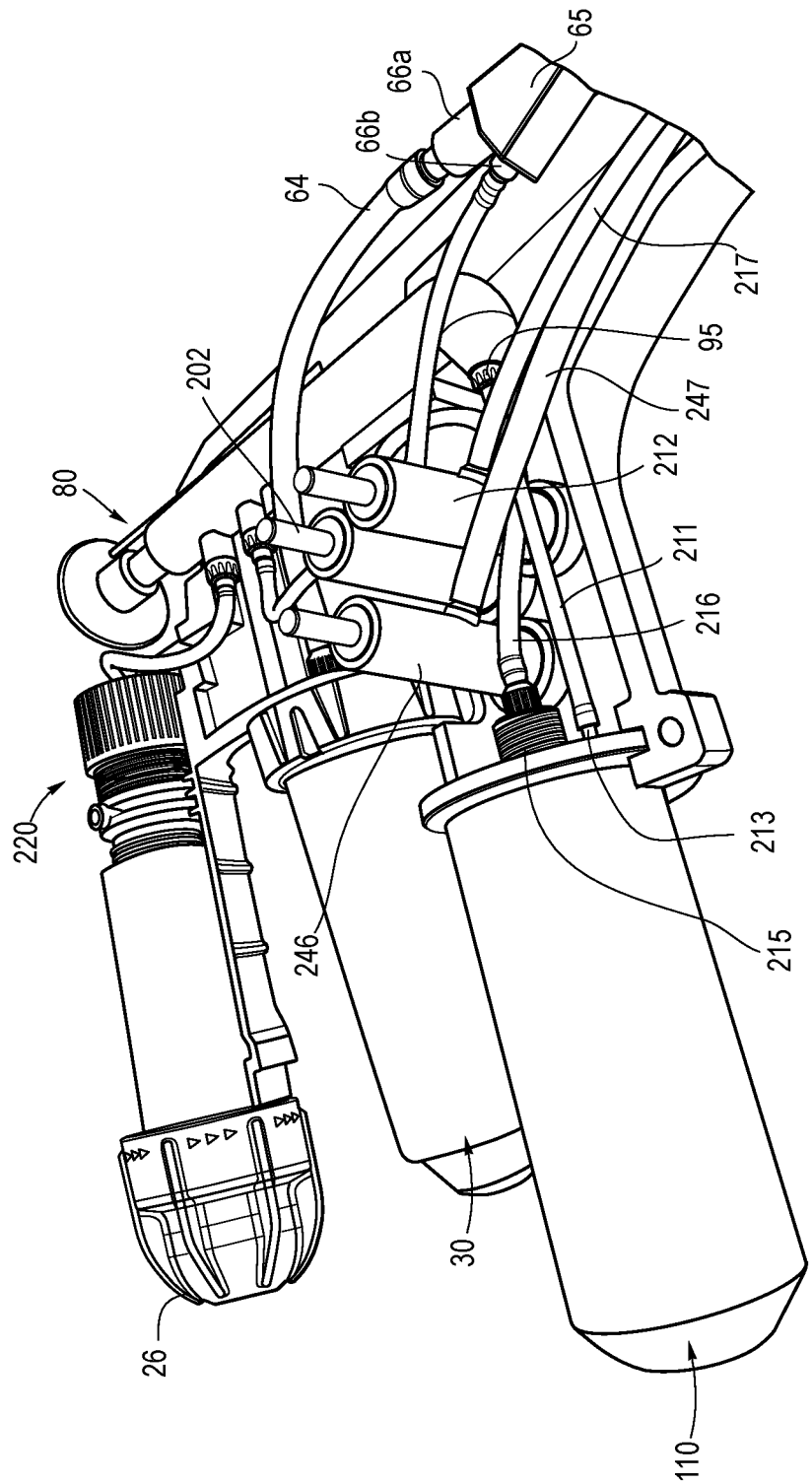
FIG. 18 is a partial perspective view of the system of FIG. 17.
Figure 19:
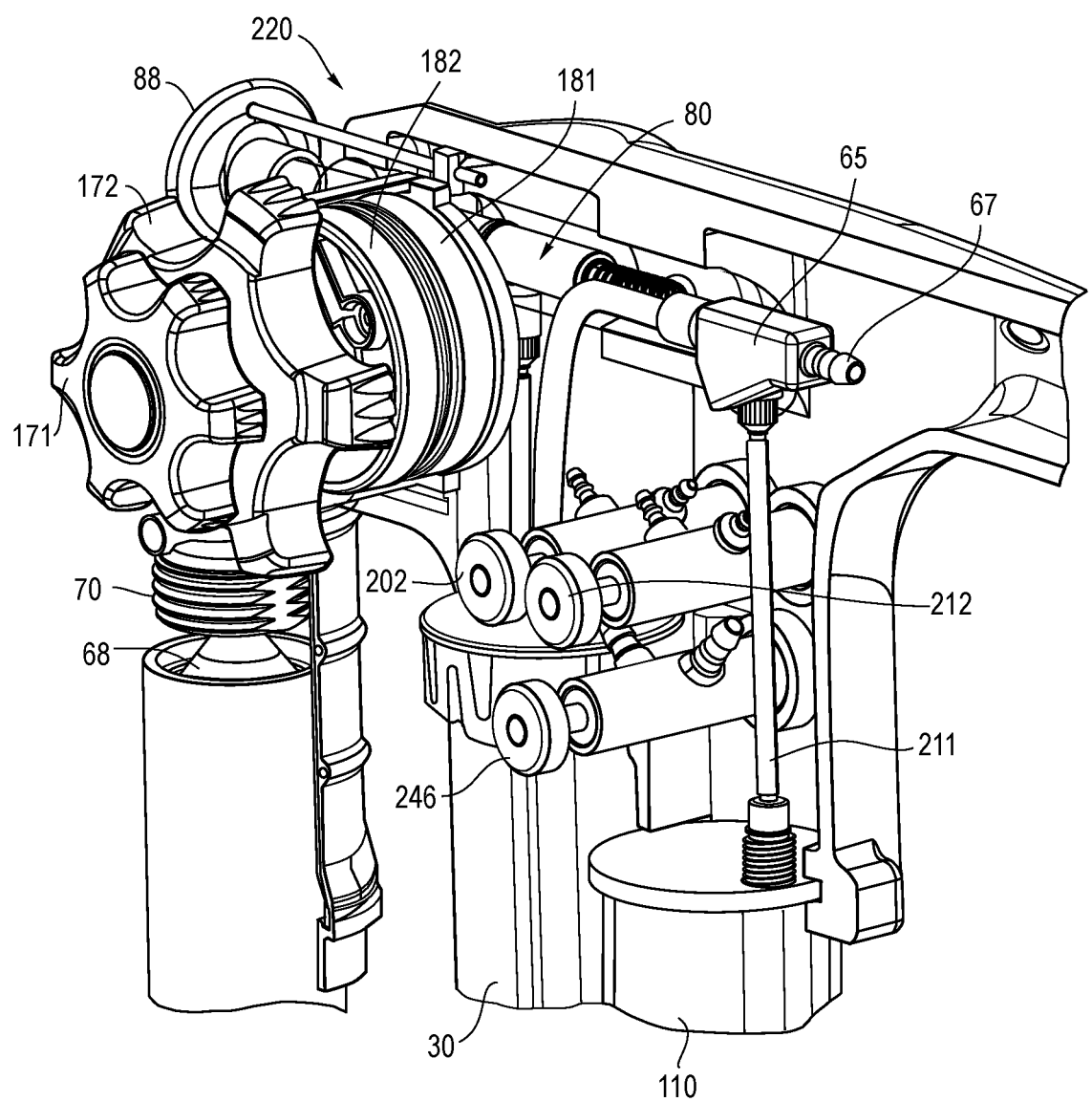
FIG. 19 is a perspective view of the system of FIGS. 17-18, with deflection wires included, and with and select tubing removed for illustrative purposes.
Figure 20:
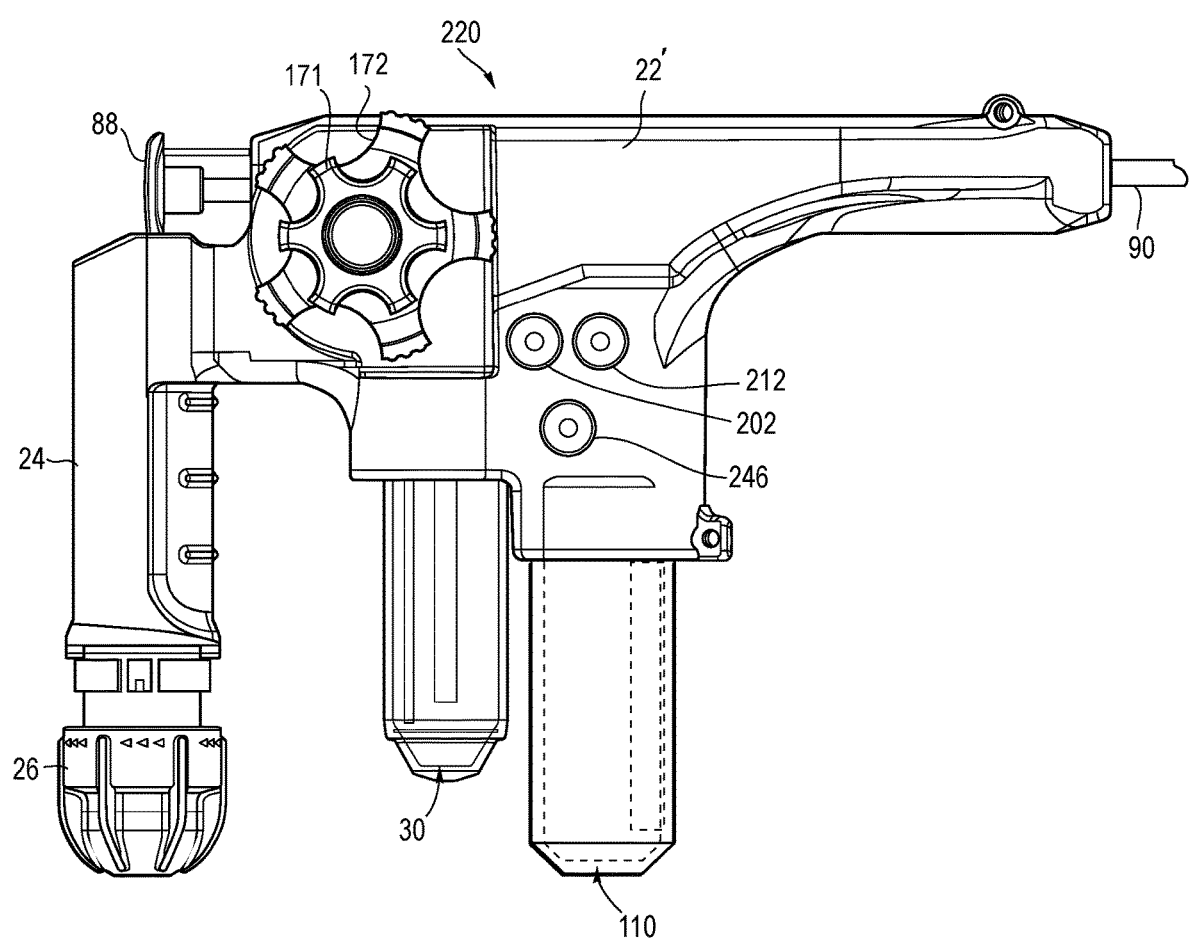
FIG. 20 is a side view of the system of FIGS. 17-19.
Figure 21:
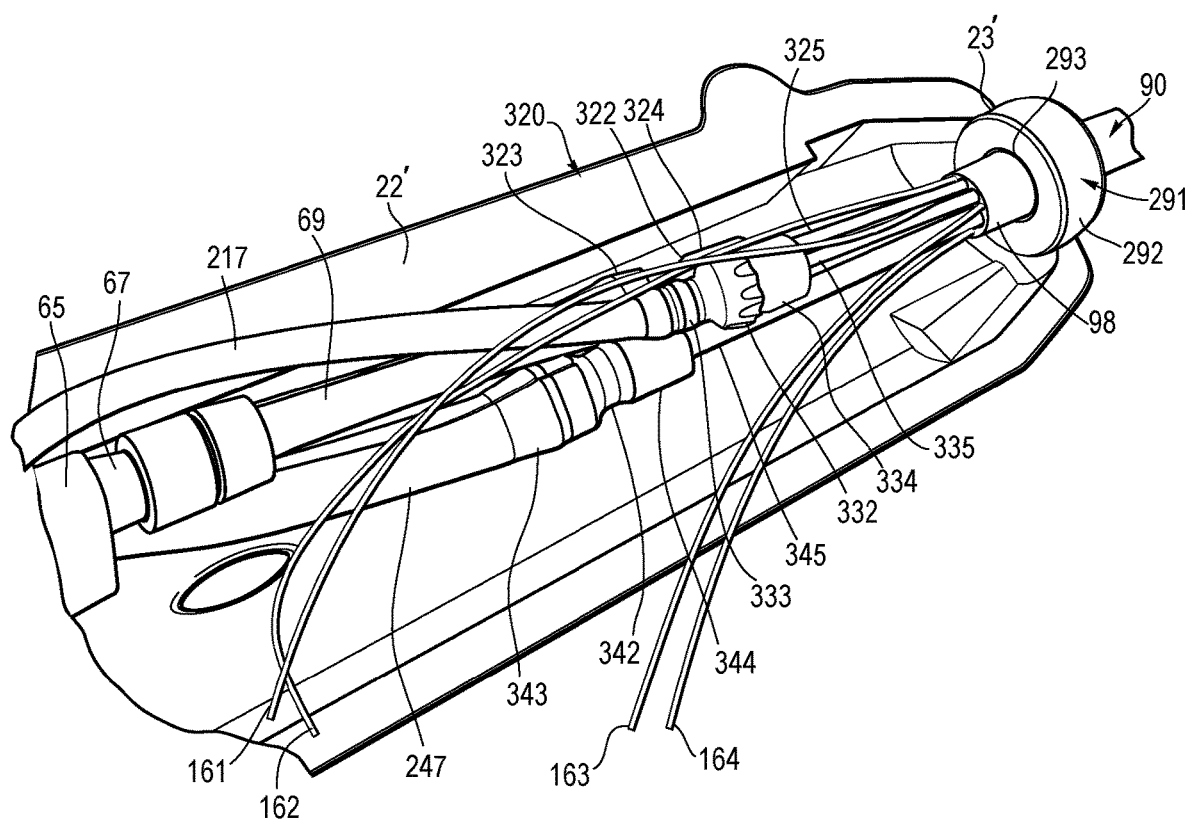
FIG. 21 is a perspective view showing features of multiple adapters between select tubing and the catheter, which may be used with the system of FIGS. 17-20.

Referring to FIG. 21, in conjunction with FIGS. 17-19, the system 220 further comprises an adapter system 320 that allows the various pieces of tubing that carry insufflation fluid or therapeutic agent, plus irrigation fluid and aspiration fluid, to be placed in fluid communication with the catheter 90. Notably, the adapter system 320 of FIGS. 17-21 is an alternative to the catheter adapter 120 described above, but the purpose of the adapter system 320 is similar as it permits multiple larger pieces of tubing to be transitioned into smaller pieces of tubing (or cannulas) that can better match the space constraints within the interior of the catheter 90.

As best seen in FIG. 17 and FIG. 21, the adapter system 320 uses multiple adapters 322, 332 and 342 between select tubing and the catheter 90. Specifically, the first adapter 322 is coupled between outlet tubing 69 (which extends from the exit port 67 of the coupler 65 as explained above) and the catheter 90. The first adapter 322 has a proximal coupling port 323 that may comprise a barbed element (similar to coupler 333 of the second adapter 332, which is easier to visualize in FIG. 21) that receives a distal end of the outlet tubing 69. A first cannula 325, which has a smaller inner and outer diameter compared to the outlet tubing 69, is secured between the first adapter 322 and the catheter 90. Specifically, a proximal end of the first cannula 325 is secured relative to an outlet region 324 of the first adapter 322, e.g., using a press-fit or other mechanical or adhesive securement. Further, a distal end of the first cannula 325 is secured within the therapeutic agent lumen 131a of the catheter 90 (seen in cross-section in FIG. 10) using a press-fit or other securement technique. In this manner, the first adapter 322 provides a transition zone that allows the therapeutic agent or insufflation fluid, originally exiting the coupler 65 via a relatively large diameter outlet tubing 69, to be guided into a smaller diameter cannula 325 that is then received into the therapeutic agent lumen 131a of the catheter 90.

Referring still to FIG. 21, the second adapter 332 is coupled between outlet tubing 217 (which extends from the valve 212 associated with irrigation fluid, as explained above) and the catheter 90. The second adapter 332 has a proximal coupling port 333 (which may have a barbed element) that receives a distal end of the outlet tubing 217, as shown in FIG. 21. A second cannula 335, which has a smaller inner and outer diameter compared to the outlet tubing 217, is secured between the second adapter 332 and the catheter 90. Specifically, a proximal end of the second cannula 335 is secured relative to an outlet region 334 of the second adapter 322, e.g., using a press-fit or other mechanical or adhesive securement. A distal end of the second cannula 335 is secured within the irrigation lumen 133a of the catheter 90 (seen in cross-section in FIG. 10) using a press-fit or other securement technique. In this manner, the second adapter 332 provides a transition zone that allows the irrigation fluid, originally exiting the valve 212 via a relatively large diameter outlet tubing 217, to be guided into a smaller diameter cannula 335 that is then received into the irrigation lumen 133a of the catheter 90.

The third adapter 342, best seen in FIG. 17 and FIG. 21, is coupled between outlet tubing 247 (which extends from the valve 246 associated with aspiration fluid, as explained above) and the catheter 90. The third adapter 342 has a proximal coupling port 343 (which may have a barbed element) that receives a distal end of the outlet tubing 247. A third cannula 345, which has a smaller inner and outer diameter compared to the outlet tubing 247, is secured between the third adapter 342 and the catheter 90. Specifically, a proximal end of the third cannula 345 is secured relative to an outlet region 344 of the third adapter 342, e.g., using a press-fit or other mechanical or adhesive securement. A distal end of the third cannula 345 is secured within the aspiration lumen 132a of the catheter 90 (seen in cross-section in FIG. 10) using a press-fit or other securement technique. In this manner, the third adapter 342 provides a transition zone that allows the aspiration fluid, originally exiting the valve 246 via a relatively large diameter outlet tubing 247, to be guided into a smaller diameter cannula 345 that is then received into the aspiration lumen 132a of the catheter 90.

In FIG. 21, it can be noted that deflection wires 161-164 are shown in a partially unassembled state, where their proximal ends are unsecured for illustrative purposes only (although, during use, they would be coupled to the deflection actuators 171 and 172 as explained in detail above) and where their distal ends extend into their respective deflection wire lumens 137a-140a of the catheter, as explained in FIG. 10 above. Further, in FIGS. 17-21, it should be noted that the camera cord 152 and the light transmitting elements for the camera are omitted for illustrative purposes only, but these components may be routed into their respective lumens 134a, 135a and 136a of the catheter 90 in the manner described in FIG. 10, above.

In the embodiment of FIGS. 17-21, the proximal end 98 of the catheter 90 may be secured relative to the housing 22' using a catheter holder 291, as best seen in FIG. 17 and FIG. 21. In one example, the catheter holder 291 comprises a generally cylindrical guide 292 having a lumen 293 extending axially therethrough. The guide 292 may comprise an outer diameter that approximates an exit opening 23' of the housing 22', as shown in FIG. 21, such that the guide 292 is held relative to the housing 22' by a friction fit and/or using adhesives or a mechanical coupling. The catheter 90 may comprises an outer diameter that approximates the size of the lumen 293 of the catheter holder 291, as depicted in FIG. 21, such that the proximal end 98 of the catheter 90 is held relative to the catheter holder 291 by a friction fit and/or using adhesives or a mechanical coupling.

Figure 22:
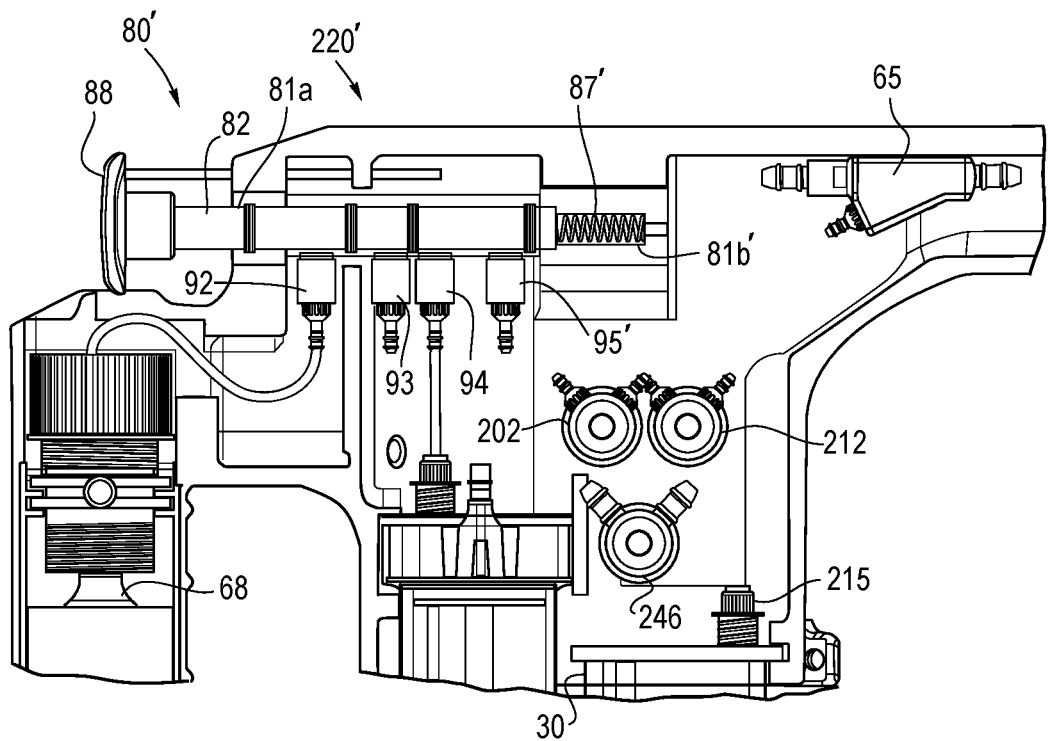
FIG. 22 is a side view of a system incorporating an alternative actuation valve assembly in which placement of an outlet port and compression spring are varied relative to the system of FIGS. 5-7.

Referring to FIG. 22, an alternative system 220' is shown having a modified actuation valve assembly 80'. In this embodiment, placement of an alternative outlet port 95' and compression spring 87' are varied, relative to their placement in the actuation valve assembly 80 of FIGS. 5-7. In particular, a distal region 81b' of the actuation valve assembly 80' comprises the outlet port 95' disposed proximal (or upstream) relative to the compression spring 87', as shown in FIG. 22. With such design, a user may have an easier time depressing the actuation button 88 since pressure may not build up as much in line with the piston 82. It should be noted that the other elements in FIG. 22 correspond generally to like parts described above, and that tubing (not shown) would be coupled to the outlet port 95' and routed to the inlet port 113 or 213 associated with the reservoir 110 holding irrigation fluid, as explained in detail above.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system suitable for delivering a therapeutic agent to a target site, the system comprising:
   a container for holding the therapeutic agent;
   a pressure source having pressurized fluid, the pressure source in selective fluid communication with at least a portion of the container;
   a catheter in fluid communication with the container and having a lumen sized for delivery of the therapeutic agent to a target site;
   a housing configured to securely retain the container; and
   a valve assembly having an inlet port and at least first and second outlet ports, wherein pressurized fluid enters through the inlet port, and in a first state the pressurized fluid is directed through the first outlet port to provide insufflation with the absence of delivery of the therapeutic agent, and in a second state the pressurized fluid is directed through the second outlet port and into the container holding the therapeutic agent to provide delivery of the therapeutic agent,
   wherein the valve assembly comprises a plunger configured for linear movement, and
   wherein the valve assembly is biased to the first state prior to movement of the plunger.

2. The system of claim 1, wherein the plunger has a generally tubular body, proximal and distal ends, a lumen extending therebetween, and first and second slots extending through a side surface of the plunger and in communication with the lumen of the plunger, wherein the first slot aligns with the inlet port in both the first and second states, and wherein the second slot selectively aligns with only the first outlet port in the first state and aligns with only the second outlet port in the second state.

3. The system of claim 2, wherein the first slot comprises a greater axial length than the second slot.

4. The system of claim 1, wherein the valve assembly comprises a third outlet port that is in selective fluid communication with a reservoir for holding an irrigation fluid, wherein in both the first and second states the pressurized fluid is directed through the third outlet port.

5. The system of claim 4, wherein an irrigation valve is disposed between the third outlet port of the valve assembly and the catheter, wherein the irrigation valve regulates when the irrigation fluid is delivered through an irrigation lumen of the catheter.

6. A system suitable for delivering a therapeutic agent to a target site, the system comprising:
   a container for holding the therapeutic agent;
   a pressure source having pressurized fluid, the pressure source in selective fluid communication with at least a portion of the container;
   a catheter in fluid communication with the container and having a lumen sized for delivery of the therapeutic agent to a target site; and
   a reservoir for holding an irrigation fluid,
   wherein the system is able to supply pressure for irrigation, insufflation, and therapeutic agent delivery; and
   a valve assembly that routes fluid for each of the irrigation, insufflation and therapeutic agent delivery states, wherein the valve assembly comprises a moveable plunger, and wherein the valve assembly is biased to a first state, prior to movement of the plunger, to provide insufflation.

7. The system of claim 6 wherein the system is able to supply pressure for each of irrigation, insufflation, and therapeutic agent delivery from the same pressure source.

8. The system of claim 6, wherein the valve assembly has an inlet port and at least first and second outlet ports, wherein pressurized fluid enters through the inlet port, and in the first state the pressurized fluid is directed through the first outlet port to provide insufflation with the absence of delivery of the therapeutic agent, and in a second state the pressurized fluid is directed through the second outlet port and into the container holding the therapeutic agent to provide delivery of the therapeutic agent.

9. The system of claim 6, further comprising a housing configured to securely retain the container, and wherein the reservoir is securely attached to the housing by an irrigation container, and wherein the irrigation fluid is delivered through an irrigation lumen of the catheter.

10. The system of claim 6, wherein the plunger is configured for linear movement.

11. A system suitable for delivering a therapeutic agent to a target site, the system comprising:
    a container for holding the therapeutic agent;
    a pressure source having pressurized fluid, the pressure source in selective fluid communication with at least a portion of the container;
    a catheter in fluid communication with the container and having a lumen sized for delivery of the therapeutic agent to a target site;
    a housing configured to securely retain the container; and
    a valve assembly having an inlet port and at least first and second outlet ports, wherein pressurized fluid enters through the inlet port, and in a first state the pressurized fluid is directed through the first outlet port to provide insufflation with the absence of delivery of the therapeutic agent, and in a second state the pressurized fluid is directed through the second outlet port and into the container holding the therapeutic agent to provide delivery of the therapeutic agent,
    wherein the valve assembly comprises a plunger having a generally tubular body, proximal and distal ends, a lumen extending therebetween, and first and second slots extending through a side surface of the plunger and in communication with the lumen of the plunger, wherein the first slot aligns with the inlet port in both the first and second states, and wherein the second slot selectively aligns with only the first outlet port in the first state and aligns with only the second outlet port in the second state.

12. The system of claim 11, wherein the first slot comprises a greater axial length than the second slot.

13. A system suitable for delivering a therapeutic agent to a target site, the system comprising:
    a container for holding the therapeutic agent;
    a pressure source having pressurized fluid, the pressure source in selective fluid communication with at least a portion of the container;
    a catheter in fluid communication with the container and having a lumen sized for delivery of the therapeutic agent to a target site;
    a housing configured to securely retain the container; and
    a valve assembly having an inlet port and at least first and second outlet ports, wherein pressurized fluid enters through the inlet port, and in a first state the pressurized fluid is directed through the first outlet port to provide insufflation with the absence of delivery of the therapeutic agent, and in a second state the pressurized fluid is directed through the second outlet port and into the container holding the therapeutic agent to provide delivery of the therapeutic agent, wherein the valve assembly comprises a third outlet port that is in selective fluid communication with a reservoir for holding an irrigation fluid, wherein in both the first and second states the pressurized fluid is directed through the third outlet port.

14. The system of claim 13, wherein an irrigation valve is disposed between the third outlet port of the valve assembly and the catheter, wherein the irrigation valve regulates when the irrigation fluid is delivered through an irrigation lumen of the catheter.

* * * * *